(12) United States Patent
Belliard et al.

(10) Patent No.: US 7,611,538 B2
(45) Date of Patent: Nov. 3, 2009

(54) INTERVERTEBRAL DISK PROSTHESIS

(75) Inventors: Karl Belliard, Bordeaux (FR); Régis Le Couedic, Andresy (FR); Jacques Senegas, Merignac (FR); Paolo Mangione, Pessac (FR)

(73) Assignee: Zimmer Spine S.A.S., Bordeaux (FR)

( * ) Notice: Subject to any disclaimer, the term of this patent is extended or adjusted under 35 U.S.C. 154(b) by 488 days.

(21) Appl. No.: 10/735,603

(22) Filed: Dec. 12, 2003

(65) Prior Publication Data

US 2005/0033435 A1    Feb. 10, 2005

(30) Foreign Application Priority Data

Aug. 4, 2003    (FR) ................... 03 09596

(51) Int. Cl.
*A61F 2/44* (2006.01)
(52) U.S. Cl. .................................. 623/17.15
(58) Field of Classification Search .... 623/17.11–17.16
See application file for complete search history.

(56) References Cited

U.S. PATENT DOCUMENTS

| 2,004,017 | A | * | 6/1935 | Stenhouse ..................... 65/329 |
| 5,562,738 | A | * | 10/1996 | Boyd et al. ............... 623/17.15 |
| 5,674,294 | A | * | 10/1997 | Bainville et al. ........... 623/17.16 |
| 5,899,941 | A | | 5/1999 | Nishijima et al. |
| 6,039,763 | A | * | 3/2000 | Shelokov ................. 623/17.16 |
| 6,113,637 | A | | 9/2000 | Gill et al. |
| 6,368,350 | B1 | * | 4/2002 | Erickson et al. .......... 623/17.14 |
| 6,395,035 | B2 | * | 5/2002 | Bresina et al. ............ 623/17.15 |
| 6,402,785 | B1 | * | 6/2002 | Zdeblick et al. .......... 623/17.16 |
| 6,419,706 | B1 | * | 7/2002 | Graf ......................... 623/17.16 |
| 6,517,580 | B1 | * | 2/2003 | Ramadan et al. .......... 623/17.15 |
| 6,554,863 | B2 | * | 4/2003 | Paul et al. ................. 623/17.11 |
| 6,569,201 | B2 | * | 5/2003 | Moumene et al. ......... 623/17.11 |
| 6,572,653 | B1 | | 6/2003 | Simonson |

(Continued)

FOREIGN PATENT DOCUMENTS

| EP | 0 699 426 A1 | 3/1996 |
| FR | 2 799 638 | 4/2001 |
| WO | WO 01/01893 A1 | 1/2001 |
| WO | WO 01/64140 A1 | 9/2001 |

OTHER PUBLICATIONS

Preliminary FR Search Report dated May 3, 2004.

(Continued)

*Primary Examiner*—Alvin J. Stewart
(74) *Attorney, Agent, or Firm*—Sprinkle IP Law Group

(57) ABSTRACT

The invention provides an intervertebral disk prosthesis. The prosthesis comprises:
  a first fixing element having both an anchoring first face for anchoring in one of the vertebrae and a co-operation second face;
  a second fixing element having both an anchoring first face for anchoring in the other vertebrae and a co-operation second face;
  a first prosthesis element having both an active first face and a co-operation second face, said co-operation faces of the first fixing element and of the first prosthesis element serving to fasten the two elements together;
  a second prosthesis element having both an active first face and a co-operation second face, said co-operation faces of the second fixing element and of the second prosthesis element serving to fasten the two elements together; and
  each of said active faces of the prosthesis elements defining at least a portion of a spherical cap that is respectively concave or convex.

14 Claims, 18 Drawing Sheets

U.S. PATENT DOCUMENTS

| | | | |
|---|---|---|---|
| 6,582,431 B1* | 6/2003 | Ray | 606/61 |
| 6,641,613 B2* | 11/2003 | Sennett | 623/17.11 |
| 6,692,495 B1* | 2/2004 | Zacouto | 606/247 |
| 6,699,292 B2* | 3/2004 | Ogilvie et al. | 623/21.15 |
| 6,706,068 B2* | 3/2004 | Ferree | 623/17.11 |
| 6,726,720 B2* | 4/2004 | Ross et al. | 623/17.13 |
| 6,749,635 B1* | 6/2004 | Bryan | 623/17.16 |
| 6,793,678 B2* | 9/2004 | Hawkins | 623/17.15 |
| 6,808,538 B2* | 10/2004 | Paponneau | 623/17.16 |
| 6,966,929 B2* | 11/2005 | Mitchell | 623/17.11 |
| 6,986,789 B2* | 1/2006 | Schultz et al. | 623/17.15 |
| 6,994,727 B2* | 2/2006 | Khandkar et al. | 623/17.15 |
| 6,997,954 B2* | 2/2006 | Zubok et al. | 623/17.15 |
| 7,001,432 B2* | 2/2006 | Keller et al. | 623/17.14 |
| 7,018,415 B1* | 3/2006 | McKay | 623/17.15 |
| 7,048,764 B2* | 5/2006 | Ferree | 623/17.15 |
| 7,066,958 B2* | 6/2006 | Ferree | 623/17.12 |
| 7,083,649 B2* | 8/2006 | Zucherman et al. | 623/17.11 |
| 7,118,599 B2* | 10/2006 | Errico et al. | 623/17.14 |
| 7,147,665 B1* | 12/2006 | Bryan et al. | 623/17.16 |
| 7,169,181 B2* | 1/2007 | Kuras | 623/17.11 |
| 7,179,294 B2* | 2/2007 | Eisermann et al. | 623/17.15 |
| 7,198,644 B2* | 4/2007 | Schultz et al. | 623/17.15 |
| 7,201,776 B2* | 4/2007 | Ferree et al. | 623/17.16 |
| 7,217,291 B2* | 5/2007 | Zucherman et al. | 623/17.15 |
| 7,273,496 B2* | 9/2007 | Mitchell | 623/17.14 |
| 7,326,250 B2* | 2/2008 | Beaurain et al. | 623/17.14 |
| 7,481,840 B2* | 1/2009 | Zucherman et al. | 623/17.15 |
| 7,494,508 B2* | 2/2009 | Zeegers | 623/17.15 |
| 7,503,935 B2* | 3/2009 | Zucherman et al. | 623/17.15 |
| 7,517,363 B2* | 4/2009 | Rogers et al. | 623/17.11 |
| 7,531,001 B2* | 5/2009 | De Villiers et al. | 623/17.14 |
| 7,537,614 B2* | 5/2009 | Baumgartner et al. | 623/17.15 |
| 7,550,009 B2* | 6/2009 | Arnin et al. | 623/17.15 |
| 7,563,286 B2* | 7/2009 | Gerber et al. | 623/17.14 |
| 7,575,599 B2* | 8/2009 | Villiers et al. | 623/17.14 |
| 7,575,600 B2* | 8/2009 | Zucherman et al. | 623/17.15 |
| 2004/0010316 A1* | 1/2004 | William et al. | 623/17.16 |
| 2004/0024462 A1* | 2/2004 | Ferree et al. | 623/17.14 |
| 2004/0133278 A1* | 7/2004 | Marino et al. | 623/17.14 |
| 2004/0138749 A1* | 7/2004 | Zucherman et al. | 623/17.11 |
| 2004/0172135 A1* | 9/2004 | Mitchell | 623/17.15 |
| 2004/0225363 A1* | 11/2004 | Richelsoph | 623/17.13 |
| 2004/0225365 A1* | 11/2004 | Eisermann et al. | 623/17.15 |
| 2005/0154462 A1* | 7/2005 | Zucherman et al. | 623/17.15 |
| 2005/0256579 A1* | 11/2005 | Keller et al. | 623/17.15 |
| 2005/0267581 A1* | 12/2005 | Marnay et al. | 623/17.14 |
| 2006/0036326 A1* | 2/2006 | Baumgartner et al. | 623/17.15 |

OTHER PUBLICATIONS

International Search Report and Written Opinion, No. PCT/FR2004/002078, dated Jan. 27, 2005.
English Translation of Written Opinion, No. PCT/FR2004/002078, dated Jan. 27, 2005.
IPRP for PCT/FR2004/002078. Feb. 6, 2006.
English Translation of the IPRP for PCT/FR2004/002078. Jul. 10, 2006.

* cited by examiner

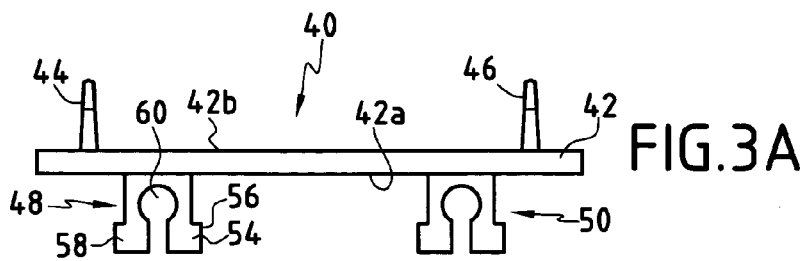
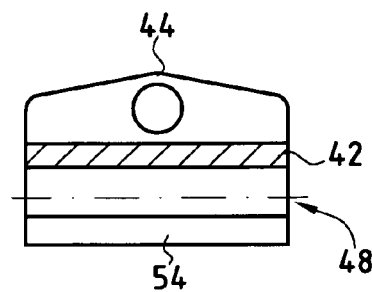
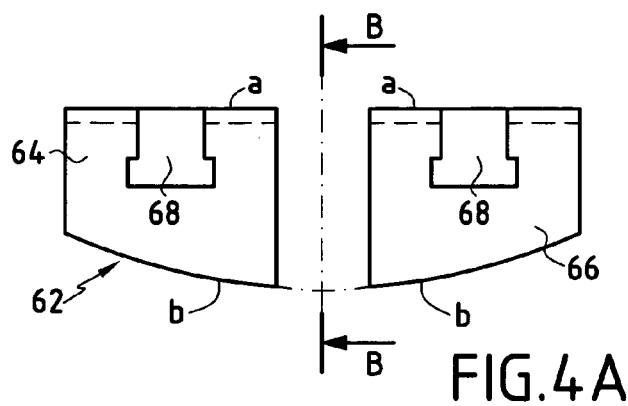
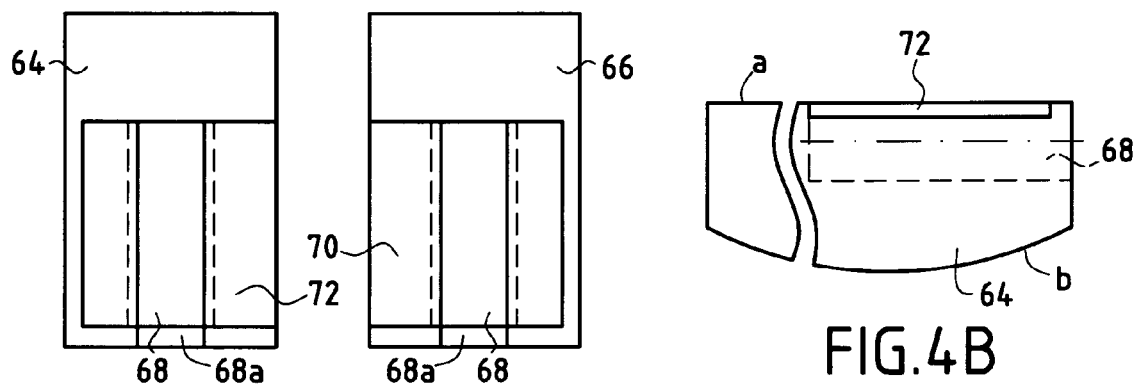
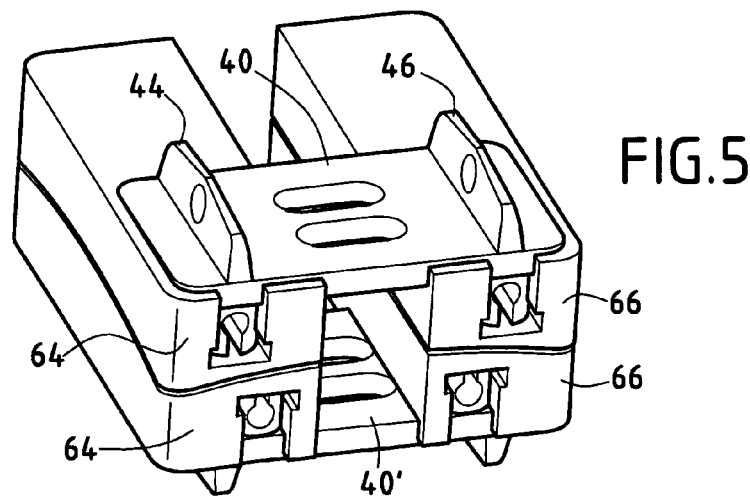

INTERVERTEBRAL DISK PROSTHESIS

The present invention relates to an intervertebral disk prosthesis and to a method of implanting said prosthesis.

BACKGROUND OF THE INVENTION

One of the pathological conditions of the vertebral column consists in degeneration of the disks that are interposed between the vertebrae of the vertebral column. This degeneration leads to a reduction in the thickness of the disk and can lead to very severe sensations of pain. When degeneration reaches an advanced stage, it is necessary to remove the natural intervertebral disk and to replace it. In the most frequent cases, a system of intervertebral spacers or cages is put into place to maintain given spacing between the vertebrae and to prevent the two vertebrae from moving relative to each other. That technique naturally presents the drawback, particularly if applied to several vertebrae, of considerably limiting the patient's ability to move.

Another possible technique consists in replacing the natural intervertebral disk with an intervertebral disk prosthesis that is mounted between the vertebrae and which, ideally, conserves for the patient all of the relative mobility between the vertebrae, or at least a large fraction thereof.

Another problem which arises with intervertebral disk prostheses is the surgical technique for putting such a prosthesis into place. Two techniques can be envisaged: an anterior technique, in which the prosthesis is put into place from the front face of the vertebral column; or a posterior technique in which the prosthesis is put into place via the outer face of the vertebral column, i.e. the face which is directly accessible. It will also be understood that when using the posterior technique, one of the major difficulties lies in the fact that the spinal cord is disposed between the outer posterior face of the vertebral column and the intervertebral plates between which the intervertebral disk prosthesis is to be placed.

Patent application EP 00/42271 describes an intervertebral disk prosthesis suitable for being put into place by the posterior technique. However, the prosthesis described in that document gives only very limited mobility (flexion-extension) between the vertebrae between which the prosthesis is installed.

OBJECTS AND SUMMARY OF THE INVENTION

A first object of the present invention is to provide an intervertebral disk prosthesis suitable for being put into place by the posterior technique and which nevertheless provides a large amount of relative mobility for the vertebrae between which the prosthesis is located.

To achieve this object, in a first aspect of the invention, the intervertebral disk prosthesis suitable for being put into place between two vertebrae by the posterior technique or by the anterior technique comprises:

a first fixing element having both an anchoring first face for anchoring in one of the vertebrae and a co-operation second face;

a second fixing element having both an anchoring first face for anchoring in the other vertebra and a co-operation second face;

a first prosthesis element having both an active first face and a co-operation second face, said co-operation faces of the first fixing element and of the first prosthesis element serving to fasten the two elements together in a plane substantially orthogonal to the axis of the vertebrae;

a second prosthesis element having both an active first face and a co-operation second face, said co-operation faces of the second fixing element and of the second prosthesis element serving to fasten the two elements together in a plane substantially orthogonal to the axis of the vertebrae; and each of said active faces of the prosthesis elements defining at least a portion of a spherical cap that is respectively concave or convex, said spherical cap portions co-operating with one another.

It will be understood that in this first aspect of the invention, the prosthesis can be put into place by the posterior technique, in particular because the fixing element of each prosthesis element is constituted by a part that is separate from the prosthesis element proper. In addition, it can be seen that the active faces in contact with each other of the two prosthesis elements are in the form of spherical caps, thus allowing physiological ball-and-socket type movements to take place between the two vertebrae.

In a first embodiment, each prosthesis element comprises two distinct parts, each active face of one of said parts defining a spherical cap portion such that the spherical cap portions belonging to the same prosthesis element are disposed on the same spherical surface when the two parts are fixed to the vertebrae by said fixing elements.

It will be understood that in this embodiment of the first aspect of the invention, each prosthesis element is constituted by two distinct parts, thus making it easier to put the prosthesis into place by the posterior technique. Nevertheless, when the two parts constituting the prosthesis element occupy their definitive position, they define an active surface that is in the form of a spherical cap.

In a second embodiment of the invention, each prosthesis element is constituted by a single part whose active face is constituted by a substantially plane surface in which a single spherical cap is formed, said spherical caps being respectively concave and convex.

In a second aspect of the invention, the intervertebral disk prosthesis suitable for being put into place between two vertebrae by the anterior technique or by the posterior technique comprises:

two prosthesis elements, each prosthesis element comprising two distinct parts, each part presenting both a first face for fixing to a vertebra and an active second face in the form of a portion of a spherical cap;

the spherical cap portions forming the active faces of the two parts belonging to the same prosthesis element being disposed on the same spherical surface when said parts are fixed to the vertebra.

It will be understood that in this aspect of the invention, each of the two prosthesis elements is constituted by two distinct parts which can thus be put into place on either side of the spinal cord. Nevertheless, once these two parts form a prosthesis element occupying its definitive position, they together define a portion of a spherical cap, thus enabling the desired ball-and-socket type movements to be obtained.

In a preferred embodiment of this second aspect of the invention, the two parts forming a prosthesis element are fixed to the vertebrae and positioned appropriately relative to each other so as to define the portion of a spherical cap with the help of a fixing element which is distinct from the two parts forming the prosthesis element. This disposition serves to reduce the size of the prosthesis element and thus to simplify putting the intervertebral disk prosthesis into place by the posterior technique.

A second object of the invention is to provide a method of implanting an intervertebral disk prosthesis of the above-defined type by a posterior technique which is particularly adapted to said prosthesis.

This object is achieved by a method comprising the following steps:

providing a posterior access to the intervertebral plate into which said prosthesis is to be implanted;

moving apart the two vertebrae defining said space;

removing the natural intervertebral disk; and implanting said prosthesis between the vertebrae by performing the following steps:

a) inserting at least one fixing element between the vertebrae round one side of the dura mater;

b) causing said fixing element to turn so as to place it beyond the dura mater in its anchoring location;

c) anchoring said fixing element in the vertebra;

d) when necessary, repeating steps a), b), and c) for the second fixing element;

e) introducing the prosthesis elements round at least one side of the dura mater; and f) causing each prosthesis element to co-operate with a fixing element.

A third object of the invention is to provide a method of implanting an intervertebral disk prosthesis of the above-defined type by an anterior technique which is specifically adapted to said prosthesis.

This object is achieved by a method comprising the following steps:

providing an anterior access to the intervertebral plate into which said prosthesis is to be implanted;

moving apart the two vertebrae defining said space;

removing the natural intervertebral disk; and implanting said prosthesis between the vertebrae by performing the following steps:

a) inserting at least one fixing element between the vertebrae;

b) anchoring said fixing element in the vertebra;

c) when necessary, repeating steps a) and b) for the second fixing element;

d) inserting the prosthesis elements between the vertebrae; and e) causing each prosthesis element to co-operate with a fixing element.

BRIEF DESCRIPTION OF THE DRAWINGS

Other characteristics and advantages of the invention appear better on reading the following description of embodiments of the invention given as non-limiting examples. The description refers to the accompanying drawings, in which:

FIG. 3A is a front view of the fixing element of a first embodiment of the prosthesis;

FIG. 3B is a side view of the fixing element of FIG. 3A;

FIG. 4A is a front view of two parts forming a prosthesis element of the first embodiment;

FIG. 4B is a view of a prosthesis element seen looking along arrow B in FIG. 4A;

FIG. 4C is a plan view of two parts constituting the prosthesis element;

FIG. 5 is a perspective view showing how the prosthesis elements and the fixing elements are assembled together;

MORE DETAILED DESCRIPTION

Figure 1:
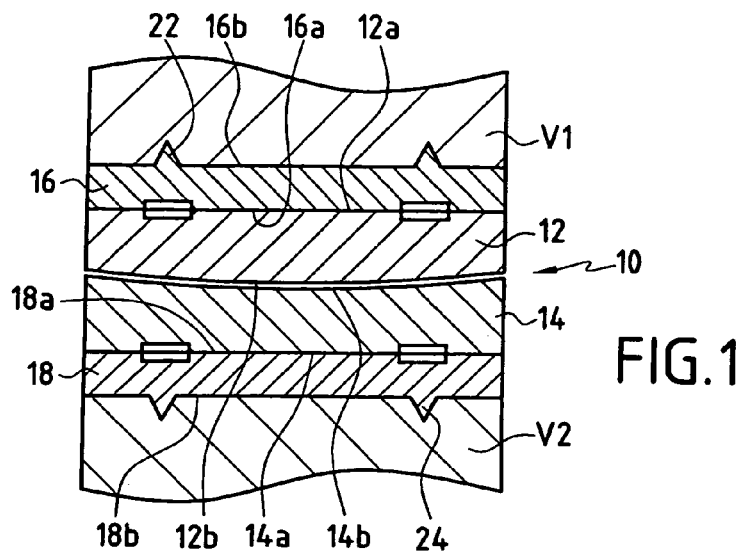
FIG. 1 is a simplified vertical section view showing the first aspect of the invention.

With reference initially to FIG. 1, there follows a description of a first aspect of the intervertebral disk prosthesis.

In this figure, there is shown in simplified manner a first vertebra V1 and a second vertebra V2 between which the intervertebral disk prosthesis 10 is to be put into place. The prosthesis 10 is constituted by a first prosthesis element 12 and a second prosthesis element 14, and by a first fixing element 16 and a second fixing element 18. The prosthesis element 12 has a co-operation face 12a and an active face 12b also referred to as a rubbing face or a contact face. This face 12b is in the form of a convex spherical cap. The prosthesis element 14 also has an active face or contact face 14b which is in the shape of a concave spherical cap and which is naturally designed to co-operate with the active surface 12b of the prosthesis element 12. As explained in greater detail below, the radii of curvature of the spherical caps 12b and 14b are not identical. The prosthesis element 14 also has a co-operation face 14a.

The fixing element 16 presents a co-operation face 16a and an anchoring face 16b. The anchoring face 16b is provided with any suitable anchoring member 22 for fixing the fixing element 12 to the plate of the vertebra V1. The co-operation face 16a of the fixing element 16 is provided with fasteners that co-operate with complementary fasteners of the face 12a of the prosthesis element 12 to fasten the prosthesis element to the fixing element, at least in a horizontal plane.

Similarly, the fixing element 18 has a co-operation face 18a and an anchoring face 18b provided with an anchoring member 24.

It will be understood that in this first aspect of the invention, because the prosthesis elements proper and the fixing elements are distinct parts, it is easier to put the intervertebral disk prosthesis into place between the vertebrae while nevertheless ensuring that it is properly secured to the vertebrae. It will also be understood that since each prosthesis element has an active face in the form of a spherical cap, the ball-and-socket type mobility between the two vertebrae is indeed recreated.

Figure 2A:
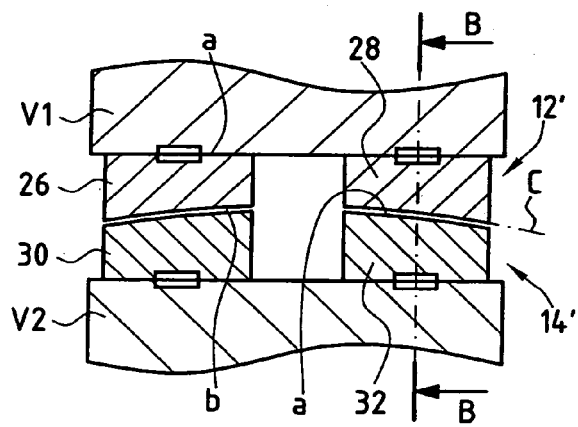
FIG. 2A is a simplified vertical section view showing the second aspect of the invention.
Figure 2B:
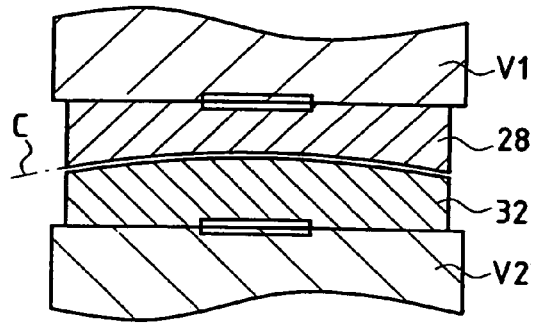
FIG. 2B is a section view of FIG. 2A on line B-B.

Reference is now made to FIGS. 2A and 2B for describing the intervertebral disk prosthesis in its second aspect.

In these figures, there can be seen the vertebrae V1 and V2 between which the prosthesis is to be put into place. The prosthesis is constituted by a first prosthesis element 12' and by a second prosthesis element 14'. Each prosthesis element 12' and 14' is constituted by two distinct parts referenced 26 and 28 for the prosthesis element 12' and 30 and 32 for the prosthesis element 14'. Each part forming the prosthesis elements has both a fixing face referenced a, and an active face referenced b. The fixing faces a of the parts 26 to 32 are provided with fasteners for engaging the vertebrae V1 and V2, these fasteners possibly being constituted by separate parts, as explained below and as shown in FIG. 1.

The active faces a of the parts constituting the prosthesis elements are defined in such a manner that they form portions of spherical caps that are respectively concave and convex. When the parts 26 and 28 forming the prosthesis element 12' are put into place on the vertebra V1, their active faces a are disposed on a concave spherical cap C. Similarly, the active faces a of the parts 30 and 32 forming the prosthesis element 14' are disposed on a spherical cap C'. As mentioned above, these spherical caps C and C' may have different radii of curvature.

It will be understood that because the two parts constituting the same prosthesis element together constitute a friction or contact surface that is in the form of a spherical cap, the same ball-and-socket mobility is obtained as in FIG. 1. In addition, because each prosthesis element is constituted by two distinct parts, it will be understood that it is easier for the surgeon to put the prosthesis element into place between the vertebrae.

With reference to FIGS. 3, 4, and 5, a first embodiment of the intervertebral disk prosthesis is described.

In FIGS. 3A and 3B, there can be seen a fixing element referenced 40. The fixing element 40 is constituted by a plate 42 having an anchoring face 42b provided with two transverse ribs 44 and 46 which constitute parts for anchoring in a vertebra. The co-operation face 42a of the plate 42 is fitted with two locking members for locking to the prosthesis element. Each of the locking members 48 and 50 is constituted by a strip 54 extending parallel to the ribs 44. The right section of each strip 54 is generally T-shaped, the strip comprising two flanges 56 and 58 in its portion that is furthest from the plate 42. In addition, in order to enable the strips to deform elastically to a certain extent, each of them has a longitudinal slot 60.

In FIGS. 4A, 4B, and 4C, there can be seen a prosthesis element 62 which is constituted by two separate parts 64 and 66. The active faces b of the parts 64 and 66 constitute portions of a spherical cap. Thus, as explained above, when the parts 64 and 66 are fixed on a vertebra, the spherical cap portions b lie on the same spherical surface. The co-operation face a of each part 64 and 66 includes an anchoring groove 68 over a fraction of its length, the right section of the groove being generally T-shaped and being dimensioned to be capable of receiving the anchoring members 48 and 50. The grooves 68 extend over a fraction only of the length of the parts 64 and 66 corresponding to the length of the anchor parts 48 and 50. In addition, and preferably, the co-operation faces a of the parts 64 and 66 include respective setbacks 70 and 72 such that when these parts are fixed on a vertebra, the plate 42 of the fixing element 40 penetrates fully into said setback. As can be seen in FIG. 4C, the grooves 68 open out via their ends 68a into end faces of the parts 64 and 66 so as to enable the locking members 48 and 50 to be inserted into the fixing element 40.

Naturally, the prosthesis as a whole has a second fixing part 40' identical to the part 40 and a second prosthesis element 62' which differs from the prosthesis element 62 solely by the fact that its active surface b defines a spherical cap that is concave.

FIG. 4 shows the two prosthesis elements constituted by the parts 64 and 66 and two other analogous parts mounted on the fixing elements 40 and 40'.

It can be seen that the fixing elements 40 and 40' in this embodiment serve not only the fix each prosthesis element to the corresponding vertebra, but also to position the two parts constituting the same prosthesis element in such a manner that their active surface does indeed constitute a spherical cap.

Figure 11:
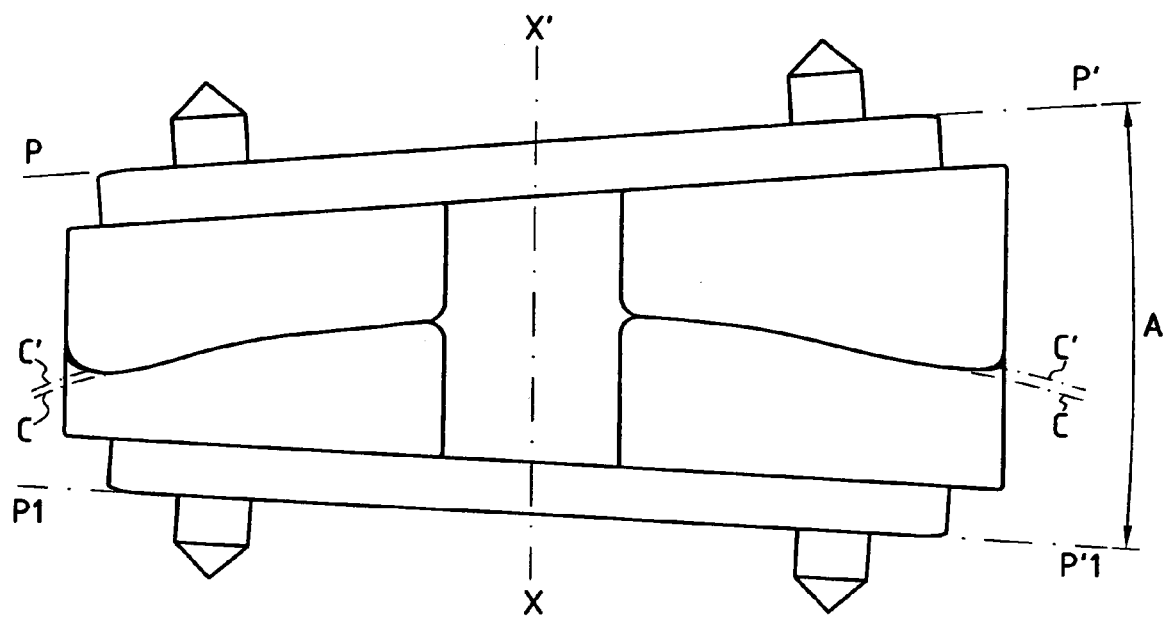
FIG. 11 shows a variant embodiment for correcting tendencies to scoliosis.

FIG. 11 shows a variant of the first embodiment of the intervertebral disk prosthesis suitable for correcting a tendency to scoliosis.

In this variant, when the prosthesis elements 64' and 66', and the fixing elements 40 and 40' are assembled together, the plates 42 of the fixing elements form between them an angle A. In order to obtain this result, the co-operation faces a of the parts 64 and 66 forming the prosthesis element 62 are disposed in a plane PP', P1P1' which is not orthogonal to the common axis XX' of the spherical caps C and C' which are constituted by the active faces of the prosthesis elements.

Figure 8:
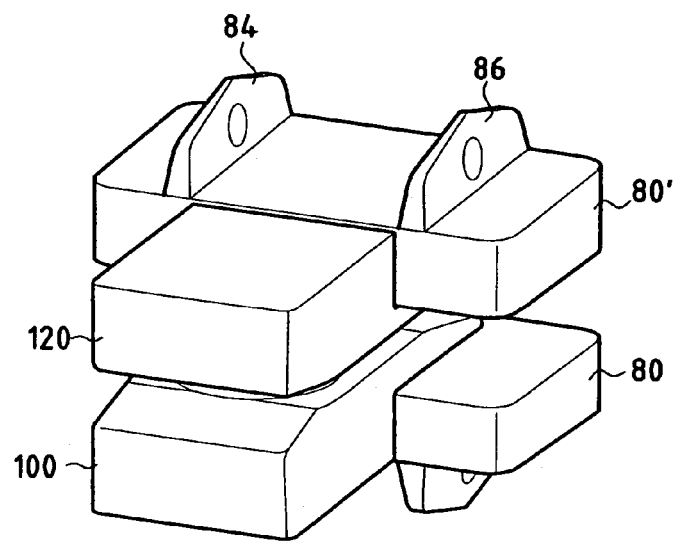
FIG. 8 is a perspective view showing how the prosthesis elements and the fixing elements of the second element of the intervertebral disk prosthesis are assembled together.

With reference now to FIGS. 6, 7, and 8, there follows a description of a second embodiment of the intervertebral disk prosthesis. In this second embodiment, each prosthesis element is constituted by a single part and each prosthesis element is fixed to the corresponding vertebra by a separate fixing element.

Figure 6A:
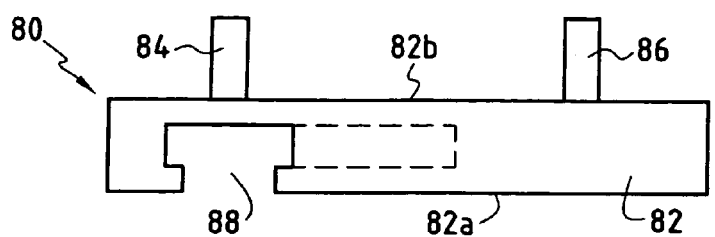
FIG. 6A is an elevation view of the fixing element in a second embodiment of the prosthesis.
Figure 6B:
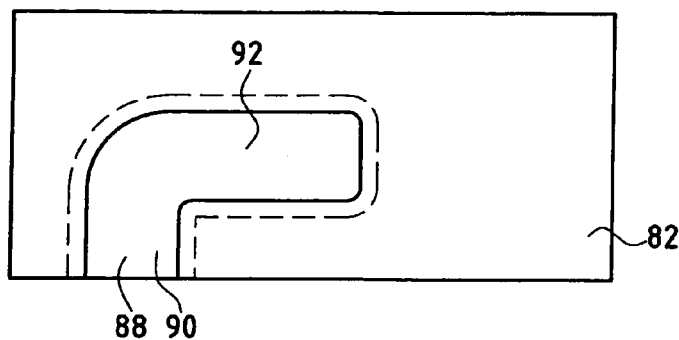
FIG. 6B is a view from below of the fixing element shown in FIG. 6A.

FIGS. 6A and 6B show an embodiment of the fixing element 80. The fixing element 80 is constituted by a preferably rectangular plate 82 that is relatively massive. The anchoring face 82b of the plate 82 is provided with members for anchoring in the vertebra constituted, for example, by two ribs 84 and 86 identical to those fitted to the fixing element 40 shown in FIG. 3. As explained below, other anchoring elements could be used.

As shown in FIG. 6B, the co-operation face 82a is provided with a locking groove 88. This locking groove has an insertion first portion 90 opening out into a long side of the plate 82 and a locking portion 92 which extends parallel to the long direction of the plate 82. As shown in FIG. 6A, the groove 88 has a right section that is T-shaped.

Naturally, the complete prosthesis has a second fixing element 80'.

Figure 7A:
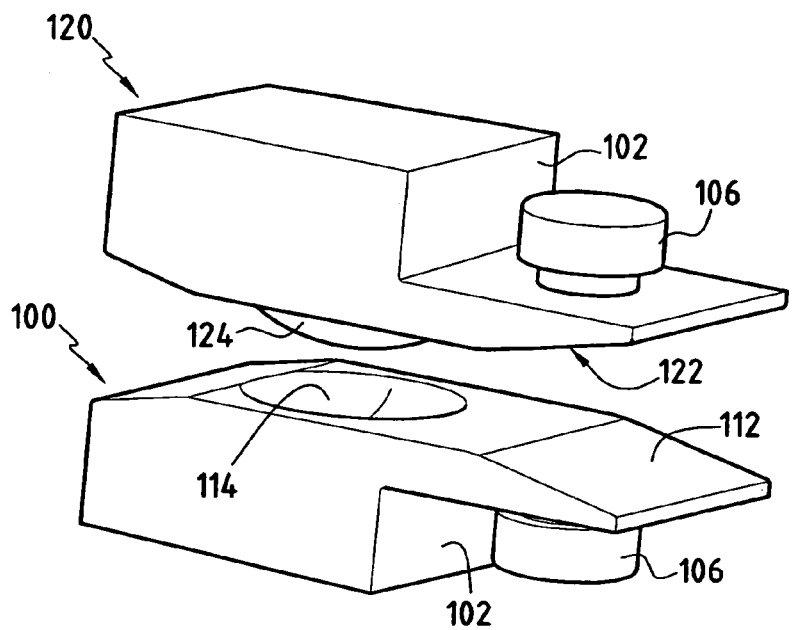
FIG. 7A is a perspective view showing the prosthesis elements of the second embodiment of the prosthesis.
Figure 7B:
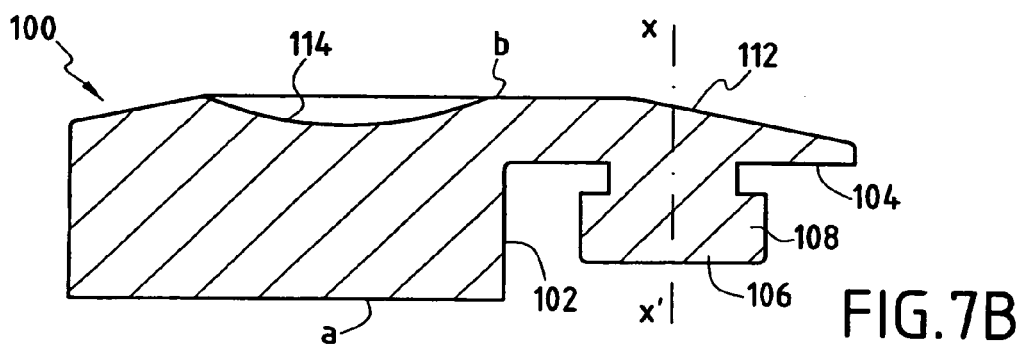
FIG. 7B is a longitudinal section view of one of the prosthesis elements of the second embodiment of the prosthesis.
Figure 7C:
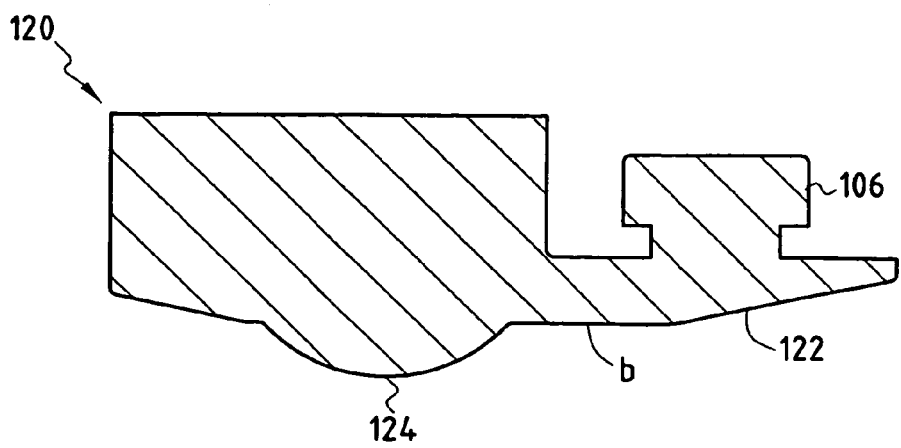
FIG. 7C is a longitudinal section view of the second prosthesis element of the second embodiment of the prosthesis.

FIGS. 7A, 7B, and 7C show the prosthesis elements of the prosthesis constituting the second embodiment. The prosthesis element 100 is constituted by a massive part whose co-operation face a presents a shoulder 102 defining a setback portion 104 with the length of the setback portion 104 corresponding to the width of the plate 82 of the fixing element 80. A locking member 106 projects from the setback portion 104. The shoulder 102 corresponds to the thickness of the plate 82. This locking member which is preferably circularly symmetrical about the axis xx' is constituted by a head 108 and a body 110. The diametral section of the locking member 108 is of a shape which corresponds to the shape of the T-groove 88 formed in the plate 82 of the fixing element 80. The active or contact face b of the prosthesis element 100 comprises a substantially plane portion 112 and a portion 114 in the form of a concave spherical cap.

The second prosthesis element 120 is identical to the prosthesis element 100 with the exception of its active face b which comprises a substantially plane portion 122 and a portion in the form of a convex spherical cap 124 suitable for co-operating with the concave spherical cap 114 of the prosthesis element 100.

In FIG. 8, there can be seen the prosthesis elements 100 and 120 mounted on the two fixing elements 80 and 80'. As can be seen more clearly in this figure, in the assembled position, the prosthesis elements 100 and 120 are orthogonal to the fixing elements 80 and 80'.

Figure 9:
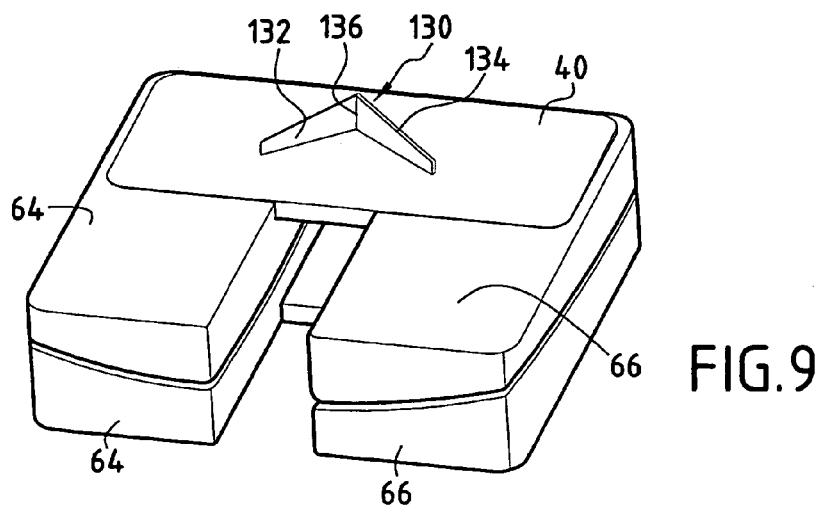

FIG. 9 shows a variant embodiment of the anchoring element provided on the anchoring faces of the fixing elements 80 or 40. In this embodiment, the anchoring elements given general reference 130 is constituted by two projecting triangular parts 132 and 134 each having one of its short sides connected to the short side of the other triangle to form an edge 136, the angle between the triangles 132 and 137 being less than 180°. This method of anchoring serves to prevent any displacement in the planes of the vertebral plates.

Figure 10:
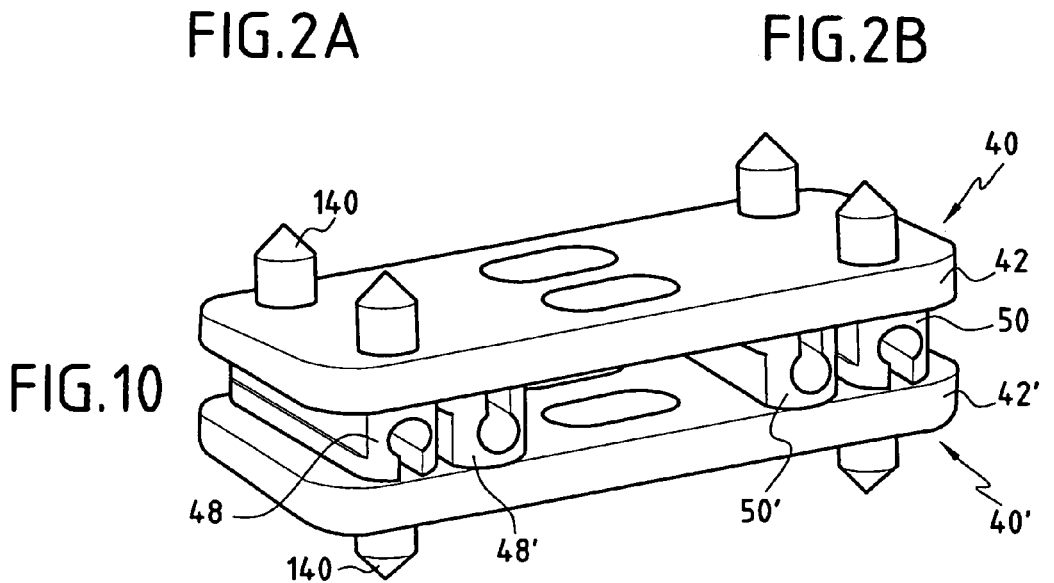
FIGS. 9 and 10 are perspective views showing variant embodiments of the members for anchoring in the vertebrae.

In FIG. 10, there can be seen another variant embodiment of the anchoring element which is in this particular case consists in four generally cylindrical studs 140 terminating in conical portions. This figure also shows that the locking members 48 and 50 of the fixing element 40 are preferably spaced further apart than the locking members 48' and 50' of the fixing element 40'. This makes it possible for the two fixing elements 40 and 40' to be placed in the configuration shown in the figure. The total thickness of the assembly constituted by the two fixing elements is thus reduced, thereby enabling them to be inserted simultaneously between the two vertebrae.

The description above relates to two embodiments of the intervertebral disk prosthesis of the invention, together with variants thereof. As mentioned above, one of the advantages of these prostheses is that they can be put into place using a posterior technique.

Figure 12A:
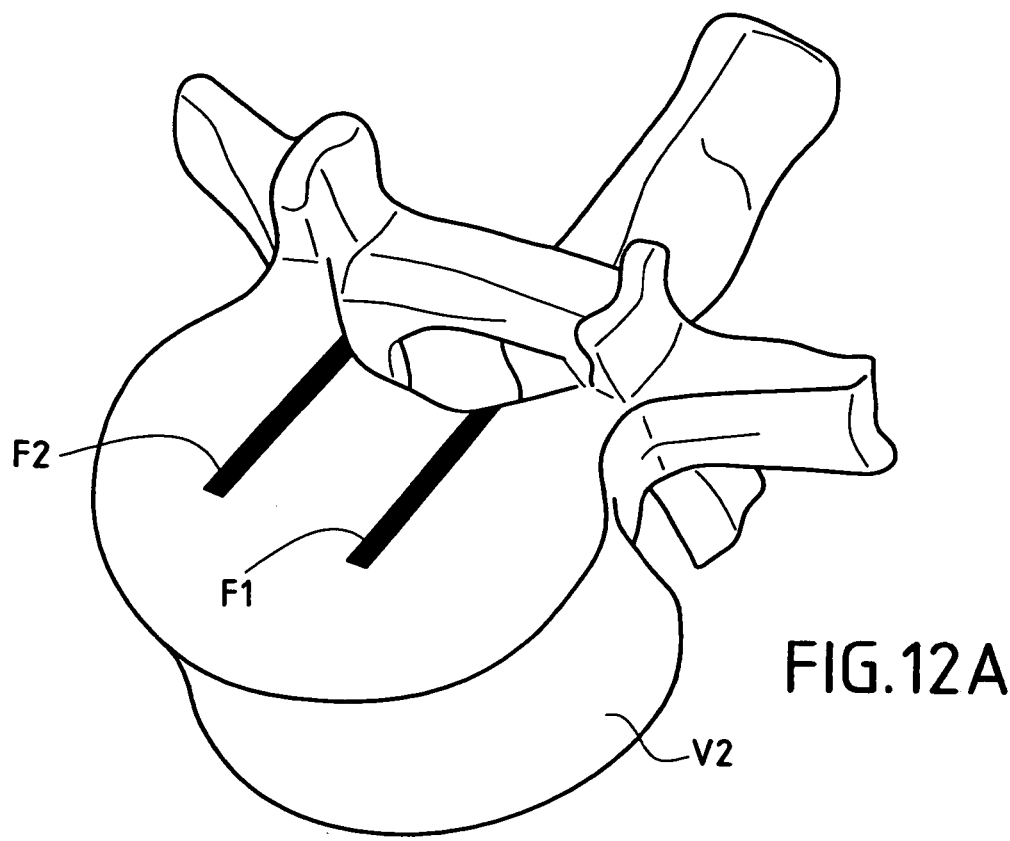
FIGS. 12A and 12B show the resections that the surgeon needs to perform in order to put the intervertebral disk prosthesis into place.
Figure 12B:
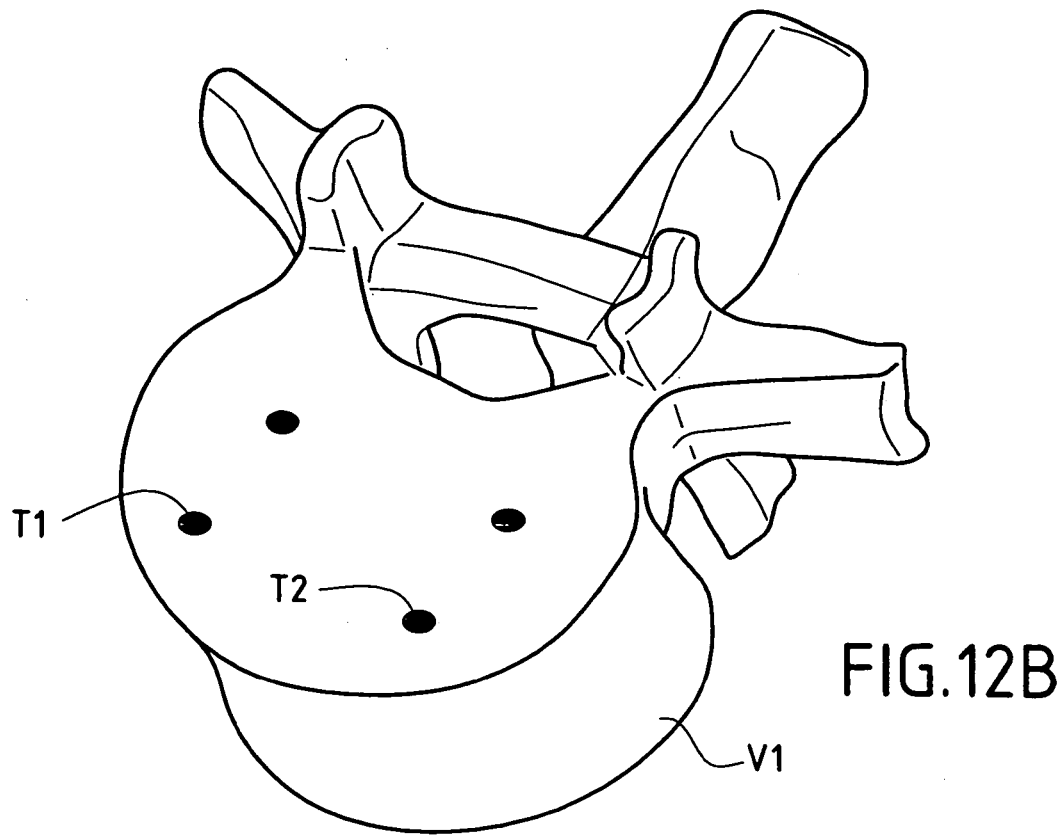

With reference initially to FIGS. 12A and 12B, there follows a description of the method of putting the prosthesis shown in FIGS. 3, 4, and 5 into place by the posterior technique.

As in the conventional posterior technique for putting intervertebral cages into place, the surgeon begins by providing posterior access to the vertebrae between which the prosthesis is to be placed: the surgeon must also move the two vertebrae apart and remove the natural disk.

Thereafter, the surgeon usually performs certain resections of portions of the two vertebrae onto which the prosthesis is to be fixed. These resections relate essentially to the epiphysis and to the facets of the vertebrae.

Functionally, the major resections are those enabling the fixing elements to be anchored to the vertebrae where that is necessary. These resections performed in the vertebral plate are of a shape that is adapted to the anchoring elements with which the fixing elements are fitted. For the rib-shaped fixing elements (FIGS. 3 and 6), these resections consist in slots F1 and F2 formed in the posterior portions of the vertebral plates (FIG. 12A). For anchoring elements in the form of pegs (FIG. 10), the resections are in the form of holes T1, T2, ... pierced in the vertebral plate (FIG. 12B). In other circumstances there is no anchoring element proper.

FIGS. 13A to 13G show a vertebral disk prosthesis of the shape shown in FIGS. 3 to 5 being put into place.

Figure 13A:
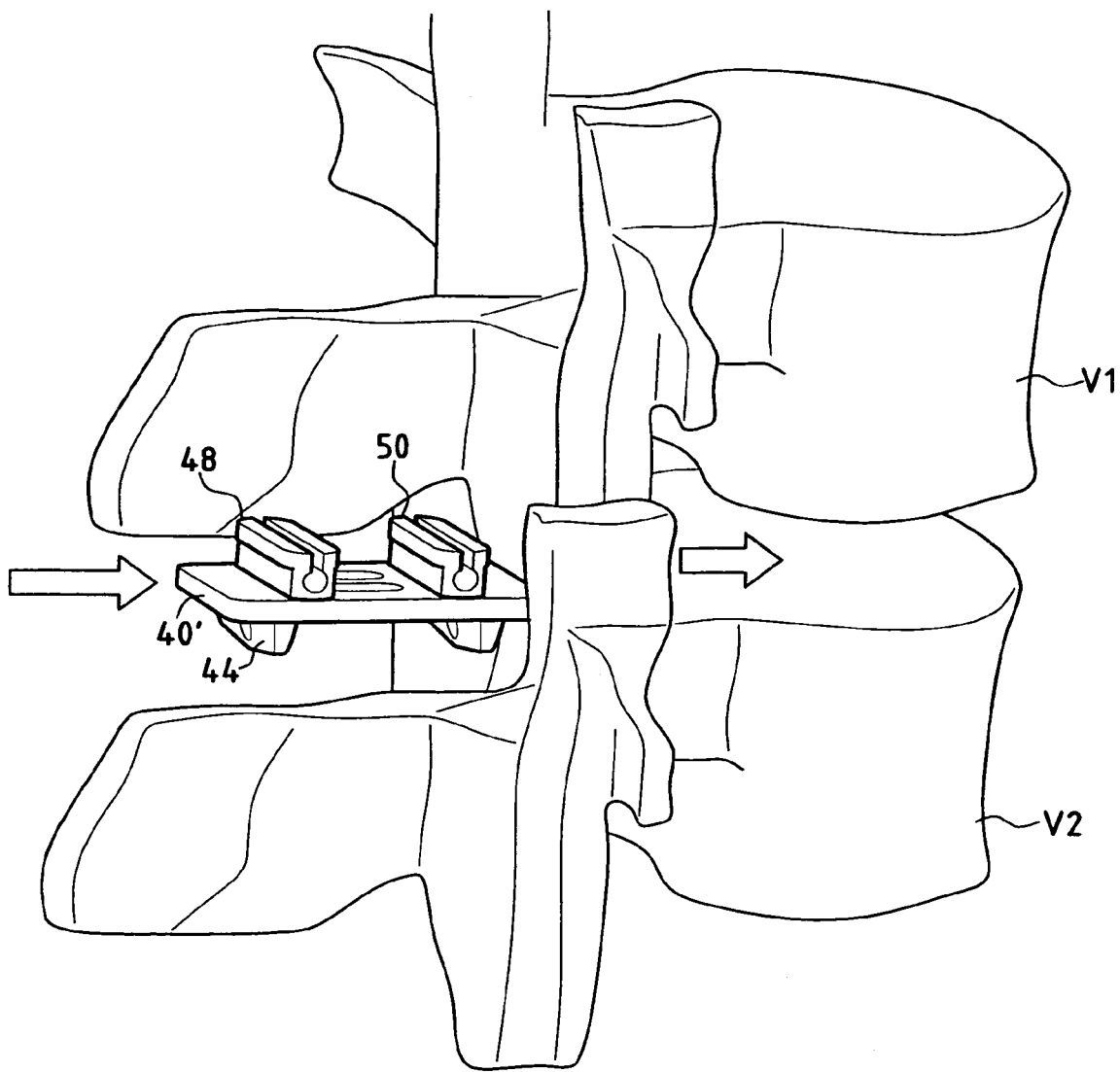
FIGS. 13A to 13G show different steps in installing a prosthesis of the type shown in FIG. 5.
Figure 13B:
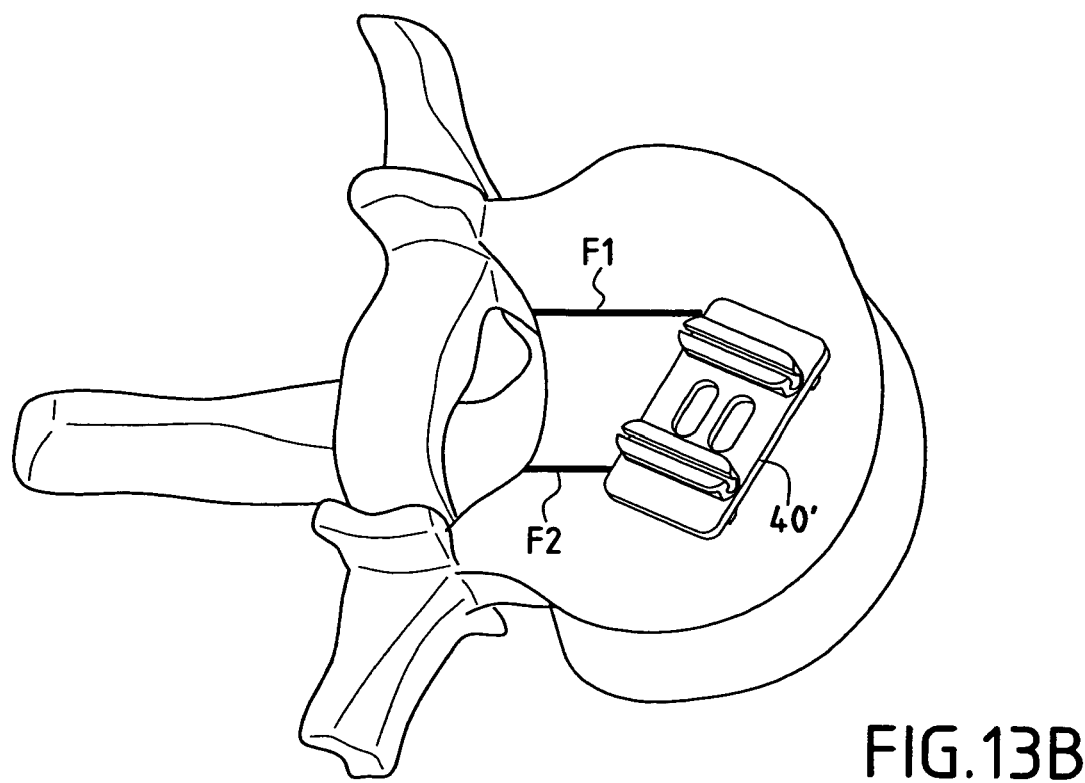
Figure 13C:
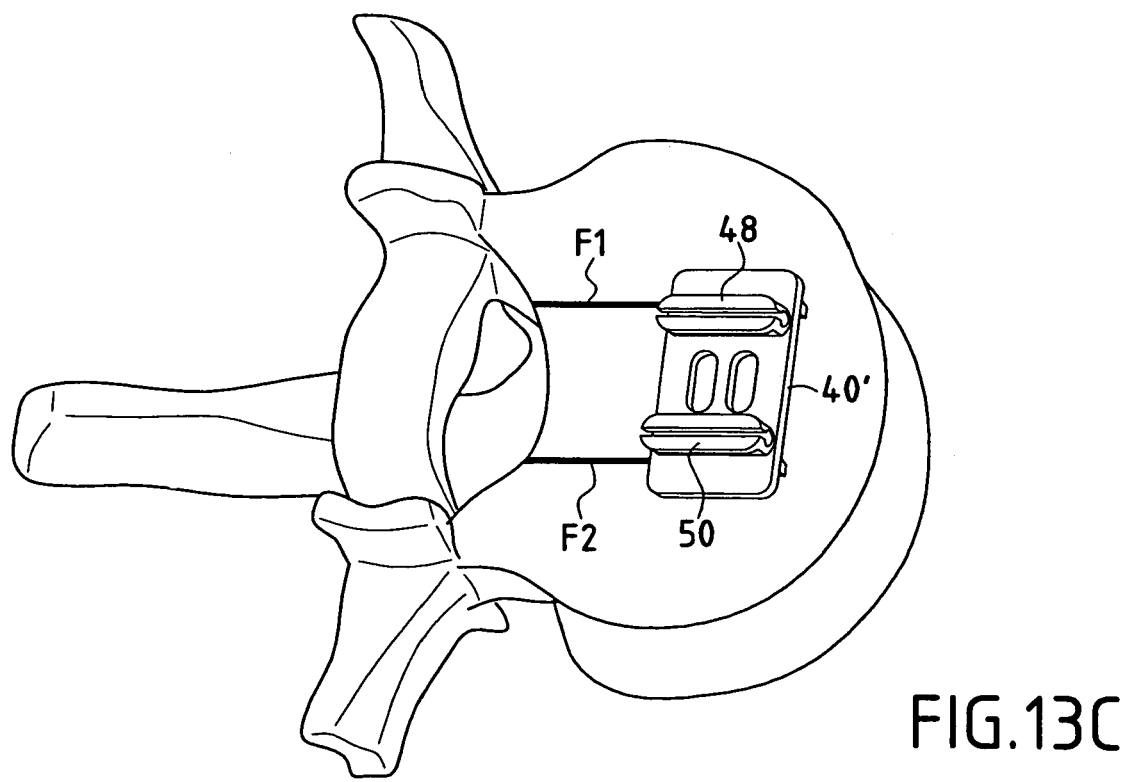
Figure 13D:
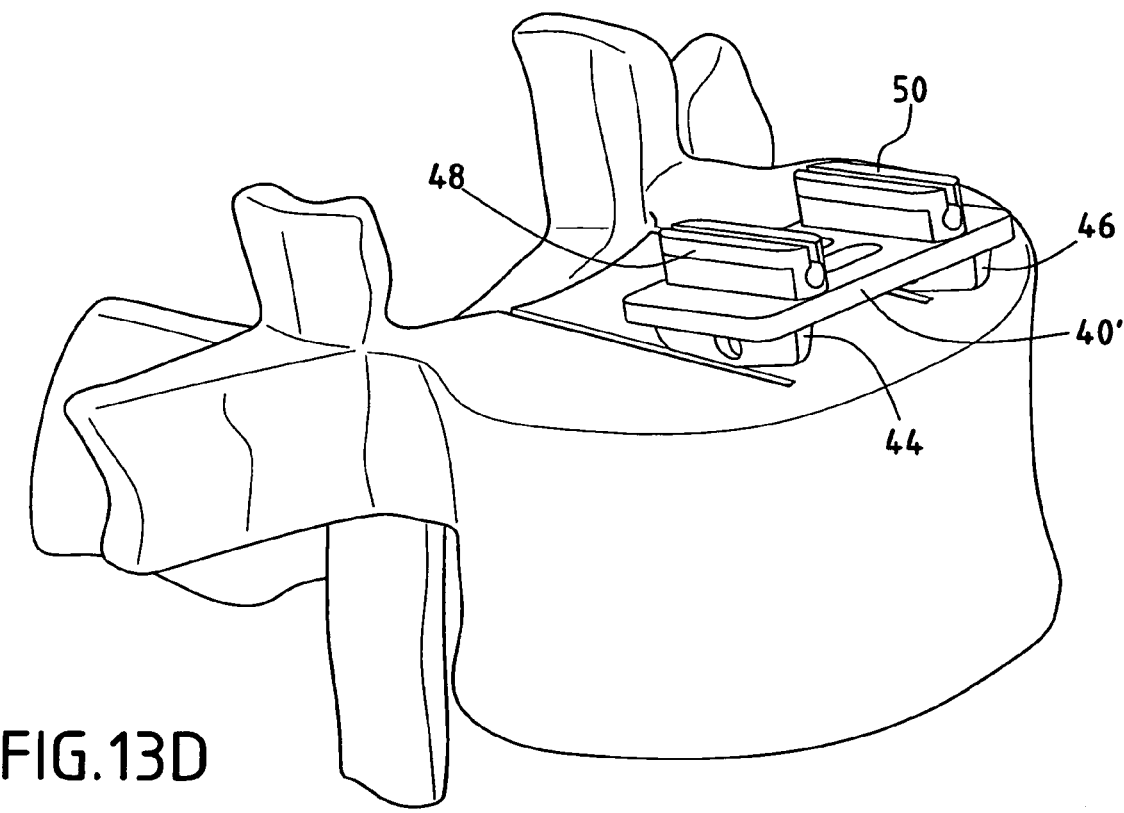
Figure 13E:
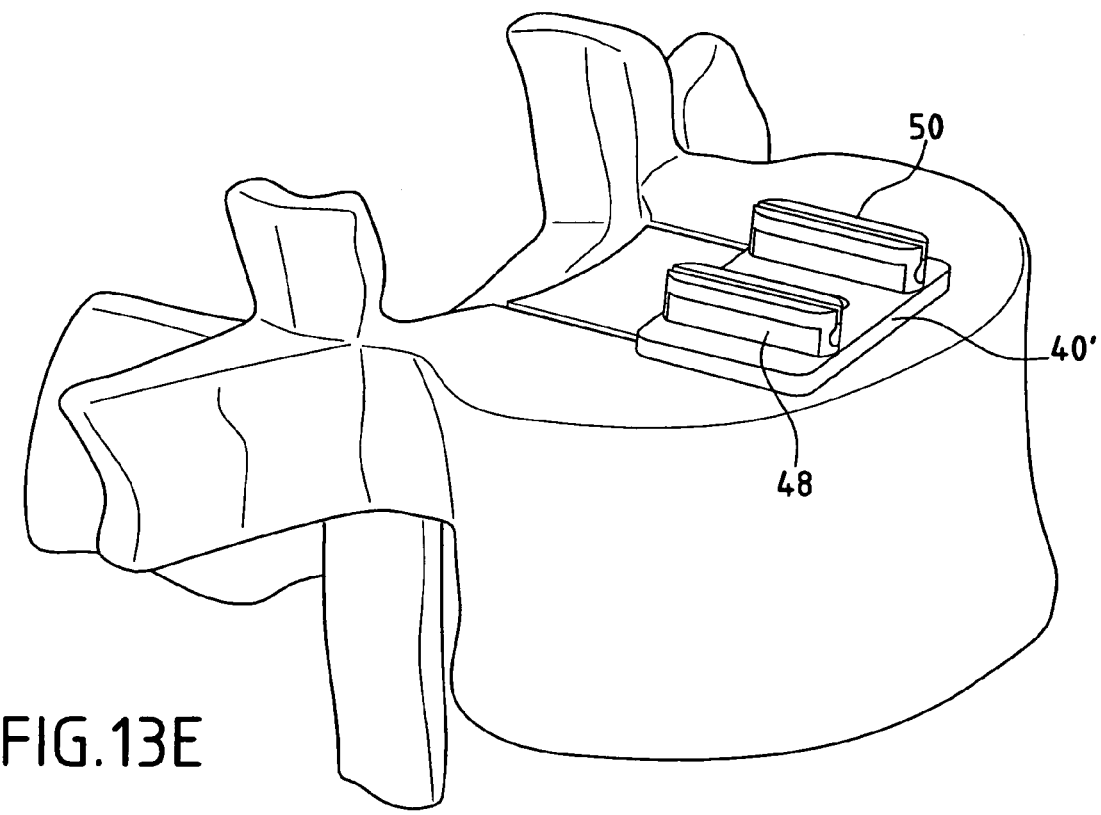
Figure 13F:
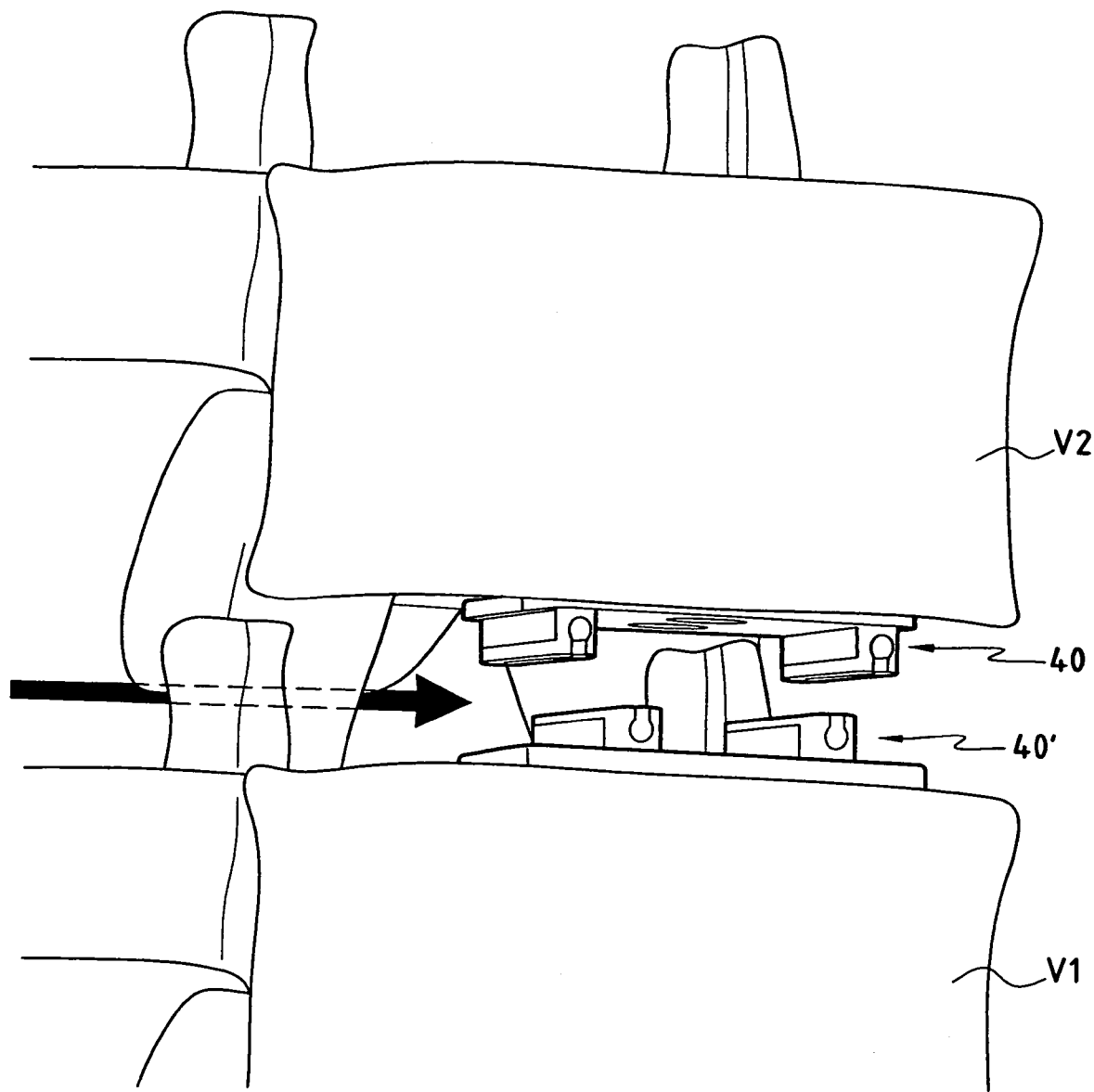

Initially, the bottom fixing element 40' is inserted between the vertebrae V1 and V2 via their posterior portions (FIG. 13A) from one side or the other of the dura mater. Then the fixing element 40' is pushed to go round the spinal cord (dura mater) (FIG. 13B) by pivoting and come into position in such a manner that the anchoring ribs are in register with the slots F1 and F2 (FIGS. 13C and 13D), after which the anchoring ribs are pushed into the slots F1 and F2 (FIG. 13E). The same process is used for putting into place the upper fixing element 40 under the upper vertebra V1.

As shown in FIG. 10, it is also possible to introduce two fixing elements simultaneously between the vertebrae and then to put them into place separately in the resections.

Still using the posterior technique, the parts 64 and 64' constituting the right-hand portions of the prosthesis elements are put into place round the right-hand side of the dura mater, going round the spinal cord.

Figure 13G:
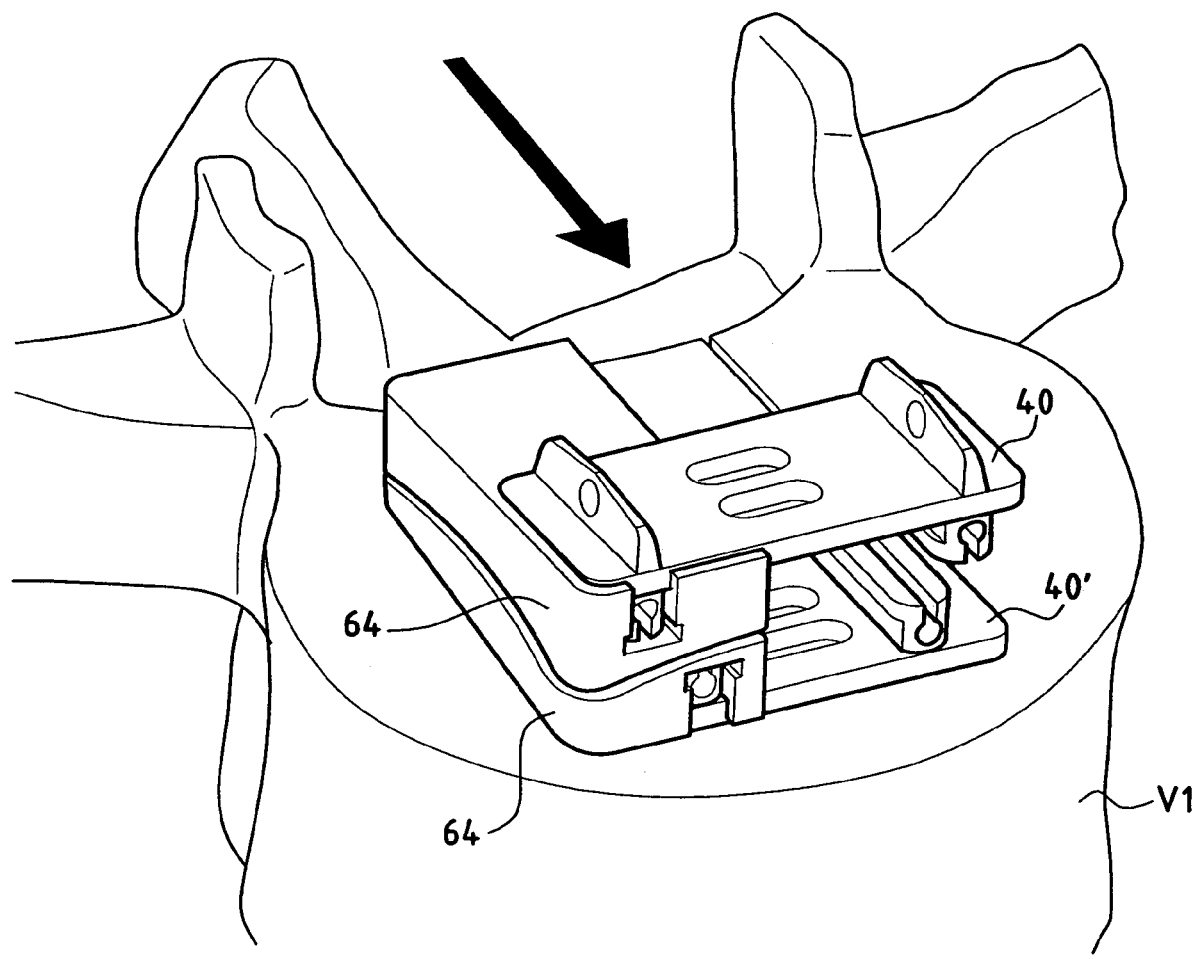

The fastening grooves 68 are engaged on the ends of the fastening strips 48 of the fixing elements. This engagement is made possible by the ability of the strips 48 to deform. The prosthesis elements are pushed until the plates 42 of the fastening elements 40, 40' penetrate into the setbacks 72 of the prosthesis parts 64 (FIG. 13G).

Finally, the same operation is performed on the parts 66 of the prosthesis elements by engaging them via the left side of the dura mater.

Figure 14A:
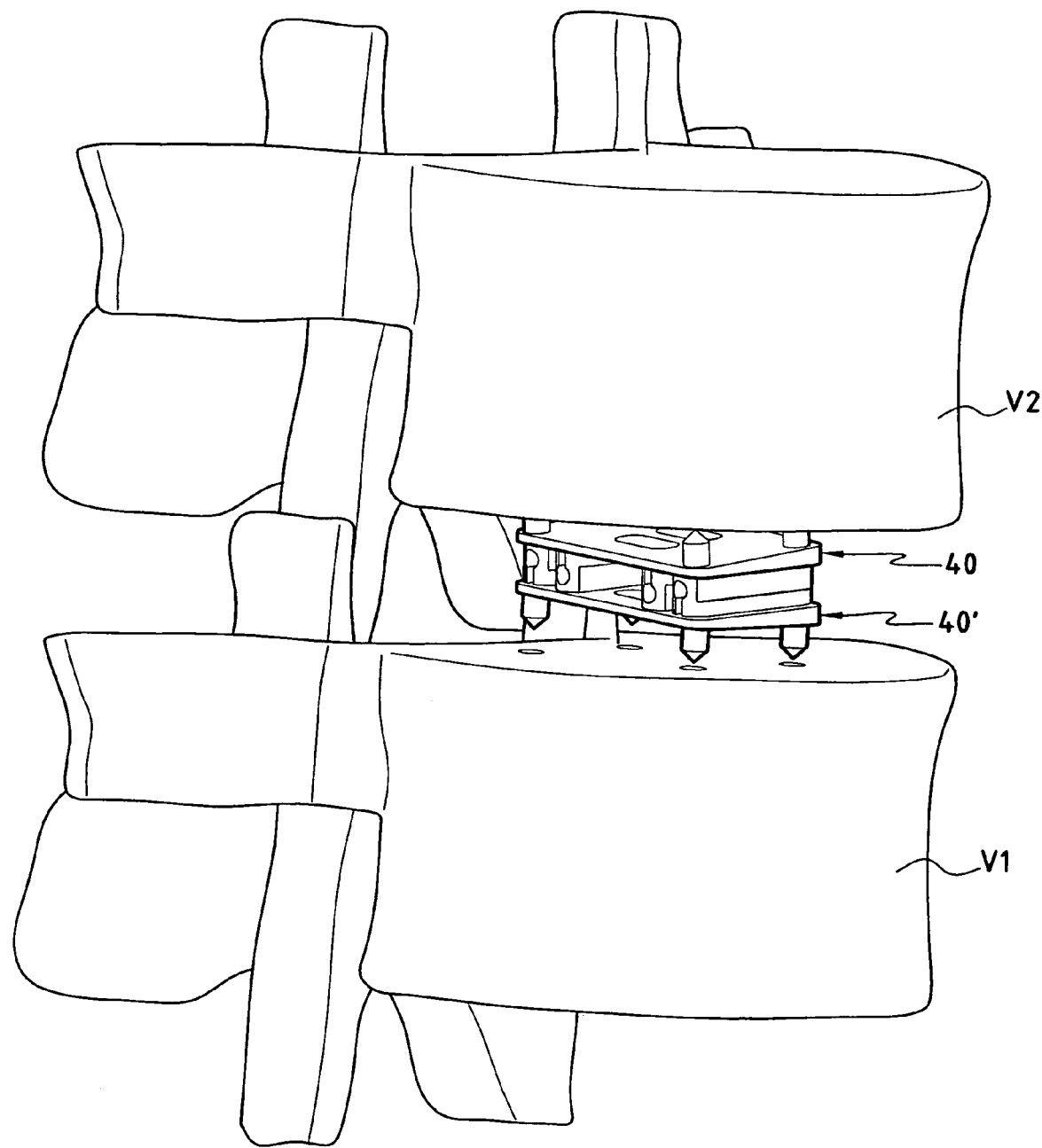
FIGS. 14A and 14B are simplified views showing steps of installing the prosthesis shown in FIG. 10.
Figure 14B:
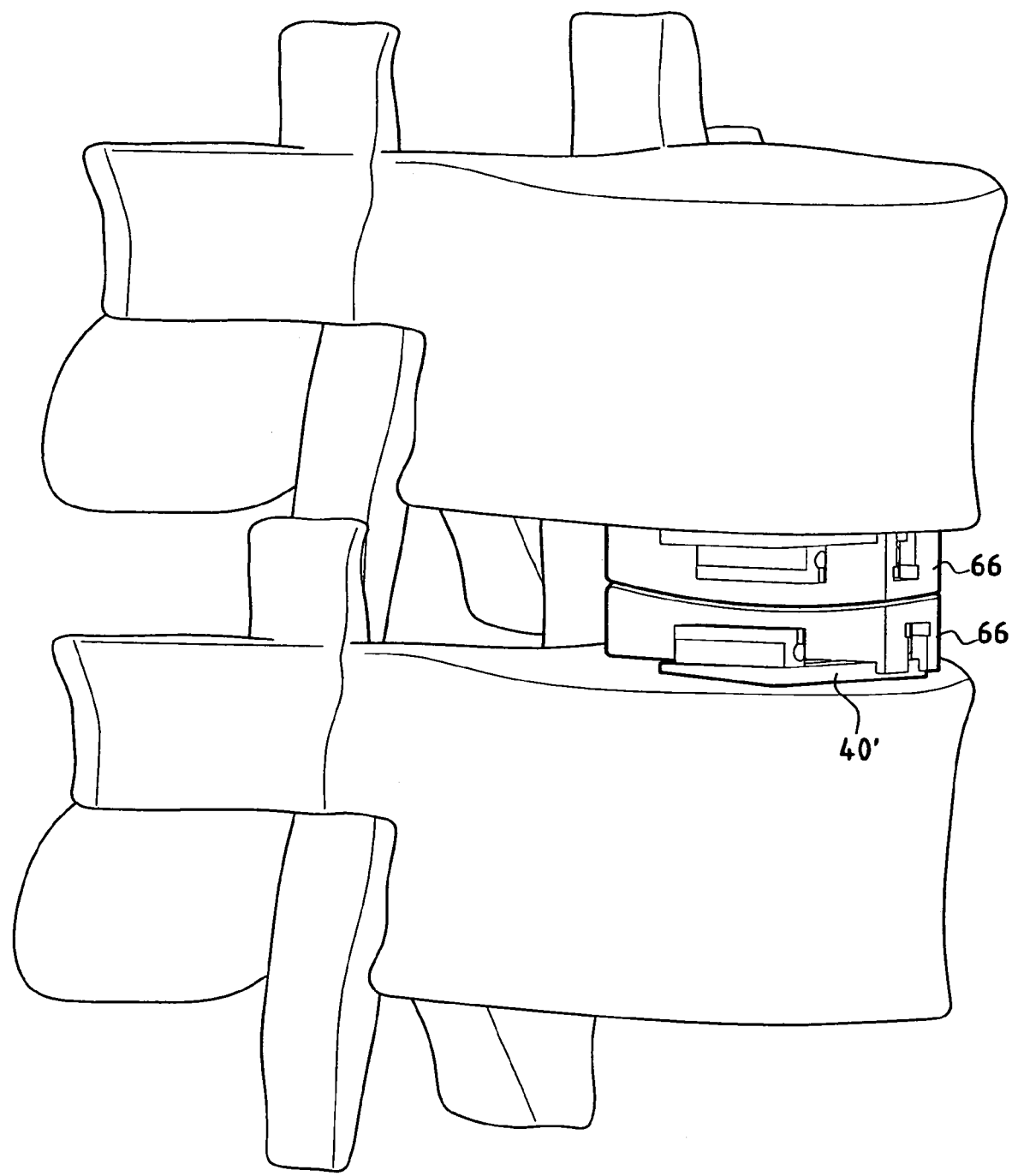

FIG. 14A shows fixing elements being inserted when they are implemented as shown in FIG. 10. FIG. 14B shows subsequent placement of the prosthesis elements.

Figure 15A:
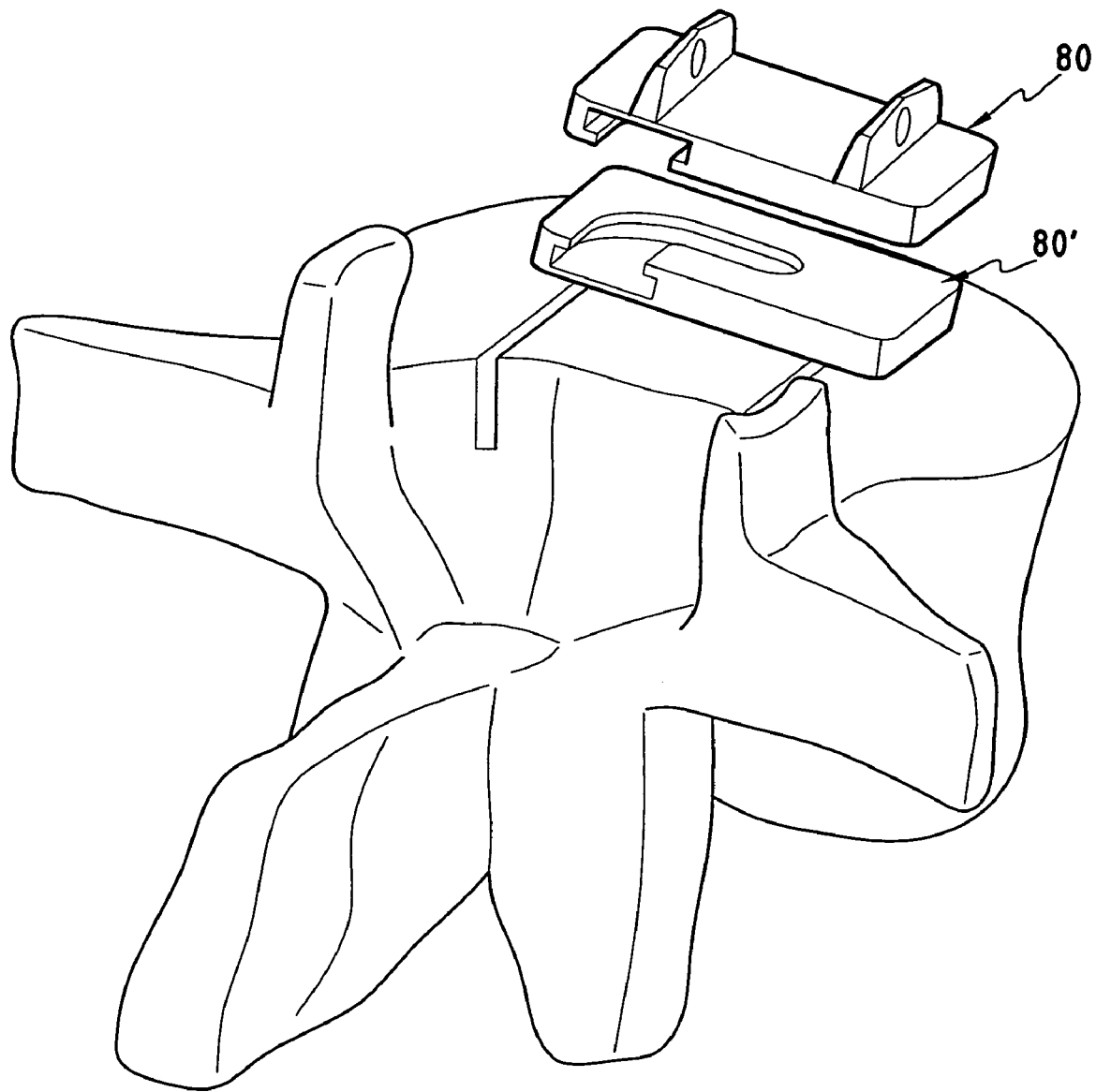
FIGS. 15A to 15C are simplified views showing steps of installing a prosthesis of the type shown in FIG. 8.
Figure 15B:
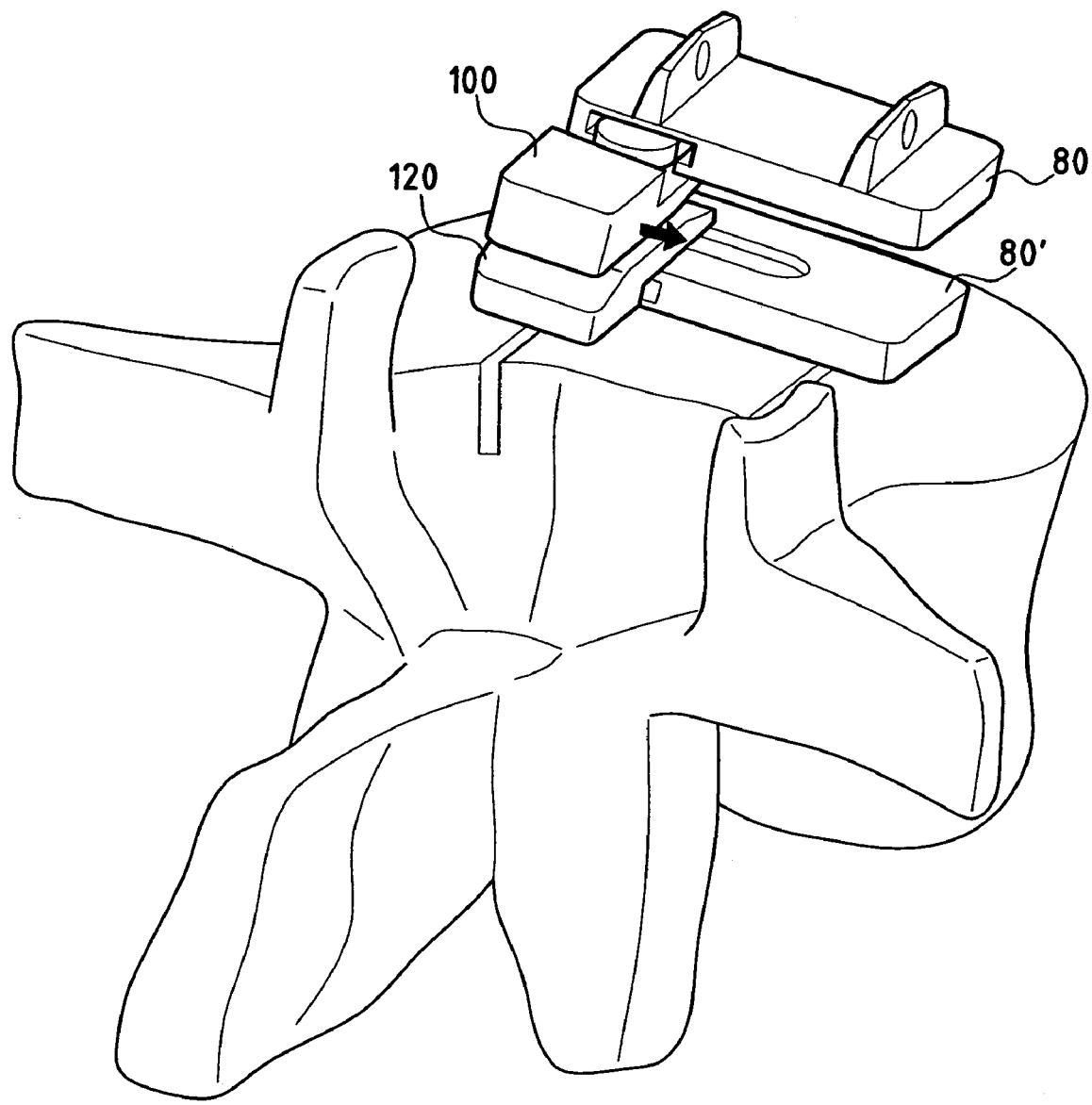
Figure 15C:
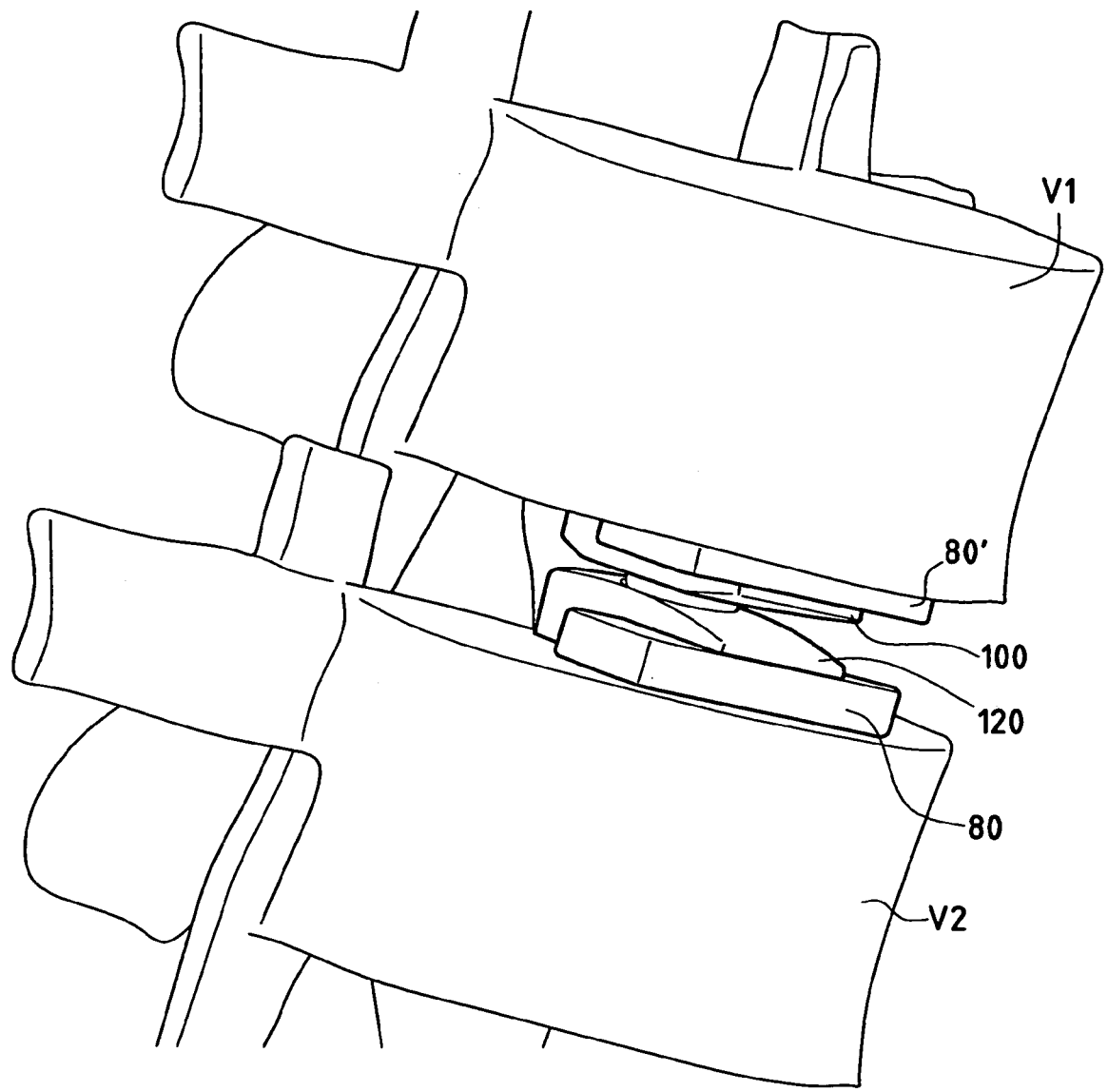

FIGS. 15A to 15C show the main steps in putting the intervertebral disk prosthesis shown in FIG. 8 into place.

FIG. 15A shows the bottom fixing element 80' being put into place by being engaged using the posterior technique round one side of the dura mater, after which this part is turned so as to put into position beyond the dura mater. This operation ends with anchoring ribs being inserted into the slots F1, F2. FIG. 15A also shows in "symbolic" manner the upper fixing element 80 put into place.

FIG. 15B shows the initial stage of putting the prosthesis elements 100 and 120 into place. In this stage, the prosthesis elements are inserted between the vertebrae on one side of the spinal cord, moving in their long direction. The locking members 106 are presented to the inlets to the first portions 90 of the locking grooves 88 in the fixing elements until they come into abutment.

Thereafter (FIG. 15C), the surgeon pushes the prosthesis elements sideways so that the locking members 106 come into abutment at the ends of the second portions 92 of the locking grooves 88. The prosthesis elements are locked to the fixing parts by co-operation between the shoulders 102 and the edges of the fixing elements.

As explained above, an important advantage of the intervertebral disk prosthesis is that it can be put into place by the posterior technique. Nevertheless, this prosthesis can naturally also be put into place by the anterior technique.

Figure 16A:
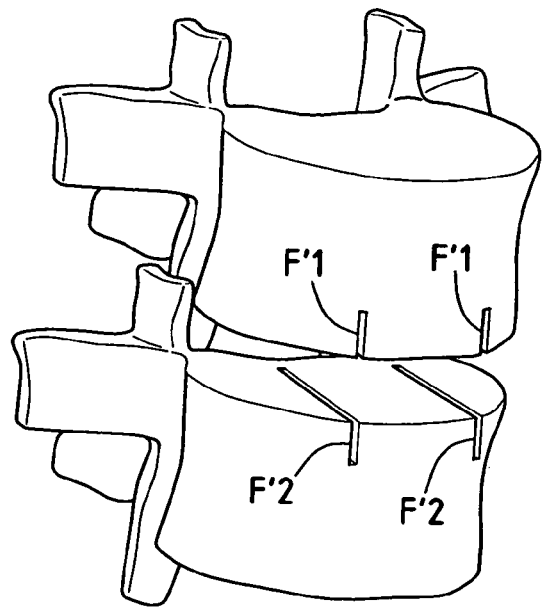
FIGS. 16A to 16C show the prosthesis shown in FIG. 5 being installed by the anterior technique.
Figure 16B:
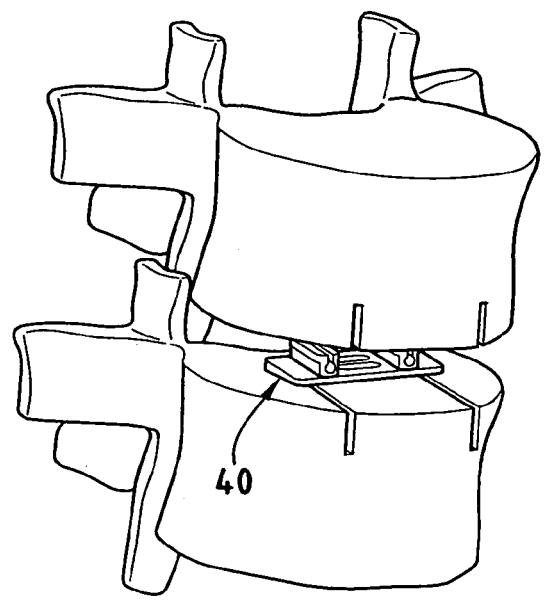
Figure 16C:
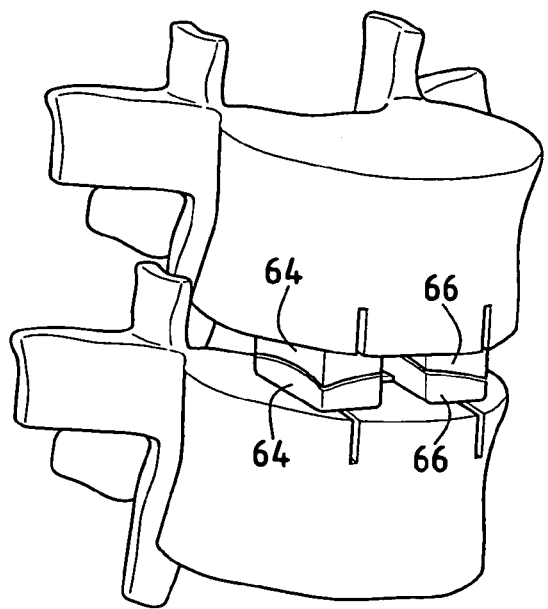
Figure 17A:
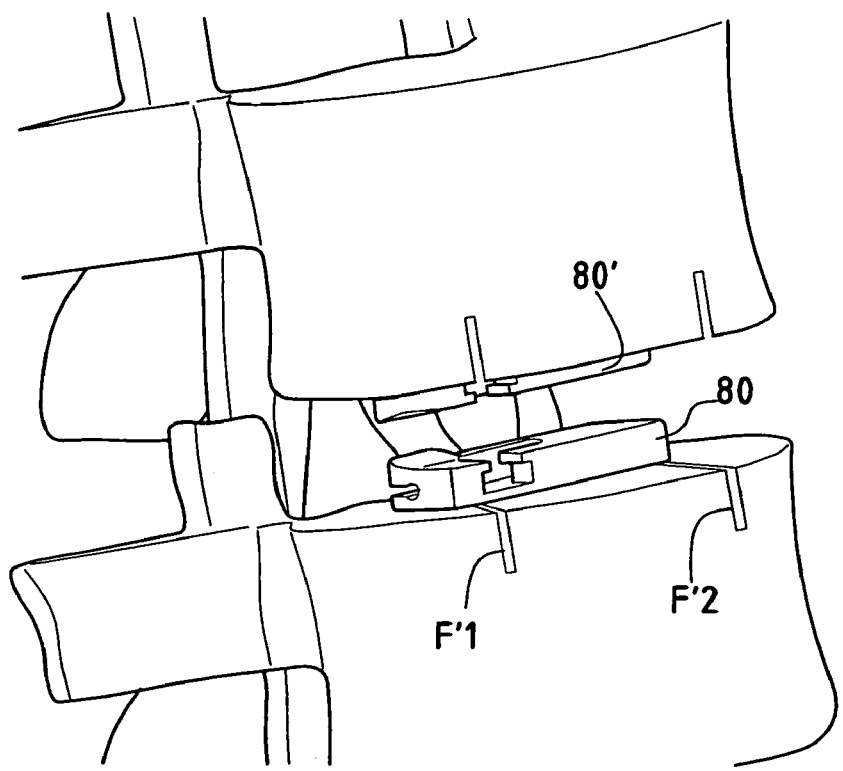
FIGS. 17A and 17B show the prosthesis shown in FIG. 8 being installed by the anterior technique.
Figure 17B:
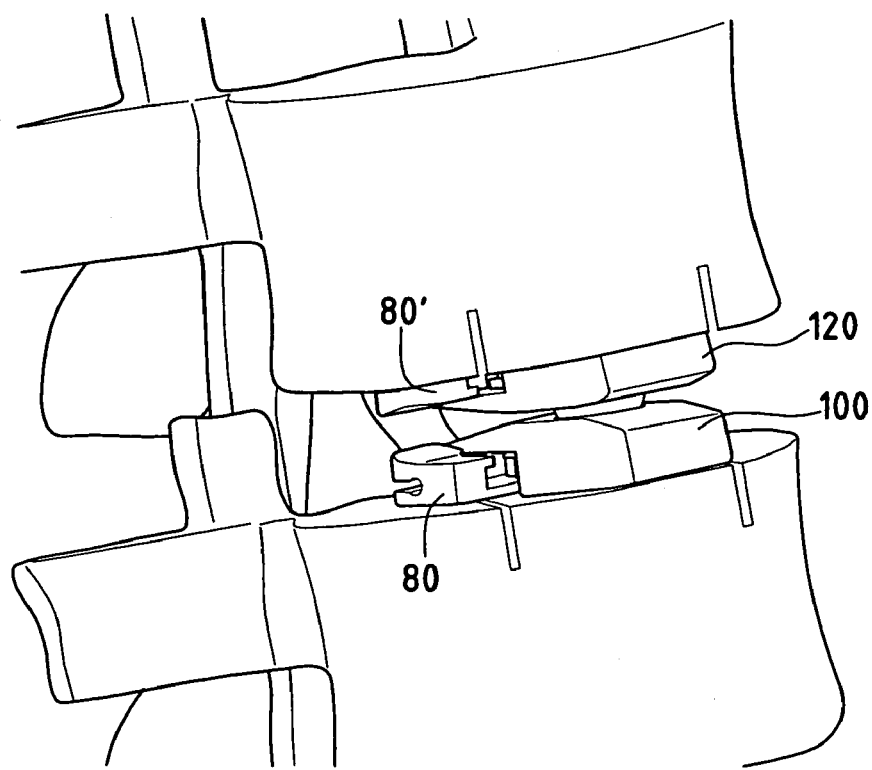

FIGS. 16A to 16C show the prosthesis shown in FIG. 5 being put into place by the anterior technique, and FIGS. 17A to 17B show the prosthesis shown in FIG. 8 being put into place by the anterior technique.

Firstly, it should be observed that the slots F'1 and F'2 are adapted to anterior placement so they open out into the periphery of the vertebral plate (FIG. 16A). Thereafter, the fixing elements 40 and 40' are put into place between the vertebrae and inserted into the slots F'1 and F'2.

Finally, the parts 26, 28, 30, and 32 forming the prosthesis elements are put into place on the fixing elements 40 and 40'.

FIG. 17A shows fixing elements 80 and 80' being put into place by the anterior technique, and FIG. 17B shows the prosthesis elements 100 and 120 being put into place on the fixing elements.

What is claimed is:

1. An intervertebral disk prosthesis suitable for being put into place between two vertebrae by the posterior technique or by the anterior technique, the prosthesis comprising:
    a first fixing element having an anchoring first face for anchoring the first fixing element to one of the two vertebrae, and a co-operation second face;
    a first prosthesis element having an active first face and a co-operation second face, the co-operation faces of the first fixing element and of the first prosthesis element, respectively, being fixed in opposition to each other such that the first fixing element and the first prosthesis element are fixed to one another in a plane substantially orthogonal to the axis of the vertebrae;
    a second fixing element having an anchoring first face for anchoring the second fixing element to in the other of the two vertebrae and a co-operation second face; and
    a second prosthesis element having an active first face and a co-operation second face, the co-operation faces of the second fixing element and of the second prosthesis element, respectively, being fixed in opposition to each other such that the second fixing element and the second prosthesis element are fixed to one another in a plane substantially orthogonal to the axis of the vertebrae;
    wherein the active first face of the first prosthesis element and the active first face of the second prosthesis element are disposed in moveable opposition to each other, one of the active first faces being concave and the other of the active first faces being convex so as to define a spherical cap,
    wherein the first prosthesis element comprises two distinct parts, each of the two distinct parts comprising the first prosthesis element having respective surfaces arranged so as to collectively define the active first face,
    wherein the second prosthesis element comprises two distinct parts, each of the two distinct parts comprising second prosthesis element having respective surfaces arranged so as to collectively define the active second face.

2. The intervertebral disk prosthesis according to claim 1, in which each prosthesis element is constituted by a single part whose active face is constituted by a substantially plane surface in which a single spherical cap is formed, said spherical caps being respectively concave and convex.

3. The intervertebral disk prosthesis according to claim 1, in which the two spherical caps are of distinct radii of curvatures.

4. The intervertebral disk prosthesis according to claim 1, in which the anchoring face of each fixing element is provided with at least one rib projecting from said face suitable for co-operating with a groove formed in the corresponding vertebra.

5. The intervertebral disk prosthesis according to claim 1, in which the anchoring face of each fixing element is provided with a plurality of studs projecting from said face suitable for co-operating with at least one recess formed in the corresponding vertebra.

6. The intervertebral disk prosthesis according to claim 1, in which the fixing face of each fixing element includes at least one portion in relief projecting from said face and suitable for co-operating with at least one recess formed in the corresponding vertebra.

7. The intervertebral disk prosthesis according to claim 1, in which the co-operation face of a fixing element or of a prosthesis element is provided with a locking member projecting from said surface, in which the other co-operation surface is provided with a hollow locking member suitable for co-operating with the projecting locking member, and in which said hollow locking member opens out into the periphery of the corresponding co-operation surface in such a manner that the projecting locking member can be engaged in the hollow locking member by movement in translation in a plane parallel to the planes of the co-operation surfaces.

8. The intervertebral disk prosthesis according to claim 1, in which the co-operating faces of the fixing elements are provided with projecting locking members for fastening them to the prosthesis elements, said locking members of one of the fixing elements being offset relative to the locking members of the other fixing elements so that the two fixing elements can be inserted between the vertebrae pressed one against the other.

9. The intervertebral disk prosthesis according to claim 1, in which each anchoring face of each fixing element includes a member for anchoring in the vertebra constituted by two right-angle triangles touching via one of their shorts sides, the two triangles not being in alignment.

10. An intevertebral disk prosthesis suitable for being put into place between two vertebrae by the anterior technique or the posterior technique, the prosthesis comprising:
    first and second fixing elements; and
    two opposing prosthesis elements, each prosthesis element comprising two distinct parts, each part of each of the two prosthesis elements having a first face for fixing to a respective one of the first or second fixing element and an active second face defining a portion of a spherical cap, wherein the respective active second faces of parts of each prosthesis element are arranged to lie on the same spherical surface when the two prosthesis elements are fixed to respective ones of the two vertebrae; and
    wherein each fixing element comprises an anchoring first face for anchoring to one of the two vertebrae and a co-operation face constructed and arranged to co-operate with the first faces of the two parts forming a respective prosthesis element so as to secure the respective two parts to the fixing element in a place substantially orthogonal to the axis of the vertebrae.

11. The intervertebral disk prosthesis according to claim 10, in which the co-operation face of either a fixing element or of a prosthesis element is provided with a locking member projecting from said surface, the other co-operation surface being provided with a hollow locking member suitable for co-operating with the projecting locking member;
    wherein the hollow locking member opens out into the periphery of the corresponding co-operation surface in such a manner that the projecting locking member can be engaged in the hollow locking member by movement in translation in a plane parallel to the planes of the co-operation surfaces.

12. The intervertebral disk prosthesis according to claim 10, wherein, when the active surfaces of the parts of the first prosthesis elements are totally facing the active surfaces of the parts of the second prosthesis elements, the co-operation surfaces of the parts forming the first prosthesis element are situated in a first plane which forms a dihedral angle with respect to the plane in which the co-operation surfaces of the parts forming the second prosthesis elements are situated, thereby enabling the prosthesis to be correct a tendency to scoliosis.

13. The intervertebral disk prosthesis according to claim 10, in which the co-operation faces of the fixing elements are provided with projecting locking members for fastening them to the prosthesis elements, said locking members of one of the fixing elements being offset relative to the locking members of the other fixing elements so that the two fixing elements can be inserted between the vertebrae pressed one against the other.

14. The intervertebral disk prosthesis according to claim 10, in which each anchoring face of each fixing element includes a member for anchoring in the vertebra constituted by two right-angle triangles touching via one of their short sides, the two triangles not being in alignment.

* * * * *